United States Patent
Gopal et al.

(10) Patent No.: US 11,324,751 B1
(45) Date of Patent: May 10, 2022

(54) DOSING REGIMENS ASSOCIATED WITH EXTENDED RELEASE PALIPERIDONE INJECTABLE FORMULATIONS

(71) Applicant: Janssen Pharmaceutica NV, Beerse (BE)

(72) Inventors: Srihari Gopal, Belle Mead, NJ (US); Raja Venkatasubramanian, Newtown, PA (US); Huybrecht T'Jollyn, Ghent (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/314,281

(22) Filed: May 7, 2021

Related U.S. Application Data

(60) Provisional application No. 63/119,382, filed on Nov. 30, 2020.

(51) Int. Cl.

| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 31/519* | (2006.01) |
| *A61K 9/00* | (2006.01) |
| *A61P 25/18* | (2006.01) |
| *A61K 47/26* | (2006.01) |
| *A61K 47/10* | (2017.01) |

(52) U.S. Cl.
CPC ......... *A61K 31/519* (2013.01); *A61K 9/0019* (2013.01); *A61K 47/10* (2013.01); *A61K 47/26* (2013.01); *A61P 25/18* (2018.01)

(58) Field of Classification Search
None
See application file for complete search history.

(56) References Cited

U.S. PATENT DOCUMENTS

| | | |
|---|---|---|
| 5,158,952 A | 10/1992 | Janssen et al. |
| 5,254,556 A | 10/1993 | Janssen et al. |
| 6,077,843 A | 6/2000 | Francois et al. |
| 6,555,544 B2 | 4/2003 | Francois et al. |
| 9,320,707 B2 | 4/2016 | François et al. |
| 9,439,906 B2 | 9/2016 | Vermeulen et al. |
| 10,143,693 B2 | 12/2018 | Gopal et al. |
| 2009/0163519 A1 | 6/2009 | Vermeulen et al. |
| 2011/0105536 A1 | 5/2011 | Lewyn-Briscoe et al. |
| 2012/0277253 A1 | 11/2012 | Sprogøe et al. |
| 2017/0281629 A1 | 10/2017 | Gopal et al. |
| 2019/0183896 A1 | 6/2019 | Sanders et al. |

FOREIGN PATENT DOCUMENTS

| | | |
|---|---|---|
| EP | 2529757 A1 | 12/2012 |
| WO | 2006/114384 A1 | 11/2006 |
| WO | 2011/053829 A1 | 5/2011 |
| WO | 2016/157061 A1 | 10/2016 |
| WO | 2016/164218 A1 | 10/2016 |

OTHER PUBLICATIONS

EU Clinical Trials Register; EudraCT No. 2017-001941-28; 2018 (Year: 2018).
Invega Sustenna® (paliperidone palmitate) extended-release injectable suspension, for intramuscular use Initial U.S. Approval, Reference ID 3657038, Nov. 1, 2014, pp. 1-56.
Sliwa et al.; "Body mass index and metabolic parameters in patients with schizophrenia during long-term treatment with paliperidone palmitate"; BMC Psychiatry; 2014; 14:52 (pp. 1-11) http://www.biomedcentral.com/1471-244X/14/52 (Year: 2014).
Andreasen, et al: "Relapse Duration, Treatment Intensity, and Brain Tissue Loss in Schizophrenia: A Prospective Longitudinal MRI Study", 2013, 609-615.
Berwaerts, et al., Efficacy and Safety of the 3-Month Formulation of Paliperidone Pa Imitate vs Placebo for Relapse Prevention of Schizophrenia A Randomized Clinical Trial, JAMA, 2015, vol. 72, 8, 830-839.
Chue, et al., A review of paliperidone palmitate, Expert Rev., Neurother 12(12), 1383-1397 (2012).
Clinical Study Report R092670PSY3004 EDMS-PSDB-6481148, Sep. 2007.
Clinical Trial: History of Changes for Study: NCT03345342 A Study of Paliperidone Palmitate 6-Month Formulation, Nov. 2017 (v1).
Clinical Trials Identifier: NCT03345342, A Study of Paliperidone Palmitate 6-Month Formulation, Nov. 17, 2017.
Clinical Trials Identifier: NCT04072575, A Study of Paliperidone Palmitate 6-Month Formulation, Aug. 28, 2019.
Clinical Trials: History of Changes for Study: NCT04072575 A Study of Paliperidone Palmitate 6-Month Formulation, Aug. 27, 2019 (v1).
Clinical Trials: History of Changes for Study: NCT04072575, A Study of Paliperidone Palmitate 6-Month Formulation, Sep. 18, 2020 (v11).
Dixon JB (2010) The Effect of Obesity on Health Outcomes. Molecular and Cellular Endocrinology; 316 (2): 104-108.
Gopal, et al: "Practical guidance for dosing and switching paliperidone palmitate treatment in patients with schizophrenia", 2009, 377-387.
Gopal, et al: Comparison of Relapse-Prevention Studies of Antipsychotic Medications Developed for Administration Daily, Once Per Month, and Once Every 3 Months. Presented at American Society of Clinical Pharmacology Annual Meeting, Miami FL Jun. 2015.
Gopal, et al: Practical guidance for dosing and switching from paliperidone palmitate 1 monthly to 3 monthly formulation in schizophrenia, 2015, 2043-2054.

(Continued)

*Primary Examiner* — Layla Soroush
(74) *Attorney, Agent, or Firm* — BakerHostetler

(57) ABSTRACT

The present invention provides a method of treating patients with long acting injectable paliperidone palmitate formulations.

18 Claims, 11 Drawing Sheets

(56) References Cited

OTHER PUBLICATIONS

Hough et al., "Paliperidone palmitate maintenance treatment in delaying the time-to-relapse in patients with schizophrenia: A randomized, double-blind, placebo-controlled study", Schiz Res., 2010, 116 (2-3), 107-117.
International Search Report re: PCT/US2016/24841 dated Jun. 24, 2016 (International Filing Date Mar. 30, 2016).
Invega Sustenna® (paliperidone palmitate) extended-release injectable suspension, for intramuscular use Initial U.S. Approval: 2006. Invega Trinza Label, 16 pages.
Invega Trinza® (paliperidone palmitate) extended-release injectable suspension, for intramuscular use Initial U.S. Approval: 2006.
Kramer et al., "Paliperidone Extended-Release Tablets for Prevention of Symptom Recurrence in Patients With Schizophrenia A Randomized, Double-Blind, Placebo-Controlled Study", J Clin Psychopharmacol. 2007 27(1):6-14.
Larco et al., "Prevalence of and Risk Factors for Medication Nonadherence in Patients With Schizophrenia: A Comprehensive Review of Recent Literature", J. Clin. Psychiatry, Oct. 2002, 892-909.
Magnusson et al., CNS Drugs, Apr. 2017, 31(4), 273-288.
Mathews et al., "Comparison of Relapse Prevention with 3 Different Paliperidone Formulations in Patients with Schizophrenia Continuing versus Discontinuing Active Antipsychotic Treatment". Neuropsychiatric Disease and Treatment. vol 2020 (16): 1533-1542, Jun. 2020.
Mathews, et al: A Comparison of Schizophrenia Relapse Rates of 3 Paliperidone Formulations, Once-Daily, Once-Monthly and Once Every-3-Month: Post-Hoc Analysis from 3 Randomized Controlled Trials. Presented at European College of Neuropsychopharmacology (ECNP) Congress, Oct. 2018, Barcelona, Spain.
Mathews, et al: A Comparison of Schizophrenia Relapse Rates of 3 Paliperidone Formulations, Once-Daily, Once-Monthly and once Every-3-Month: Post-Hoc Analysis from 3 Randomized Controlled Trials. Presented at Canadian Psychiatric Association's 68th Annual Conference, Sep. 2018, Toronto, Canada.
Mathews, et al: A Comparison of Schizophrenia Relapse Rates of 3 Paliperidone Formulations, Once-Daily, Once-Monthly and once Every-3-Month: Post-Hoc Analysis from 3 Randomized Controlled Trials. Presented at Schizophrenia International Research Society Meeting (SIRS), 6th Biennial Conference, Apr. 2018, Florence, Italy.
Nasrallah H (2003) A Review of the Effect of Atypical Antipsychotics on Weight. Psychoneuroendocrinology; 28(1): 83-96.
Osborne, et al., Health-related quality of life advantage of longacting injectable antipsychotic treatment for schizophrenia: a time trade-off study, Health and Quality of Life Outcome5 2012, 10:35, pp. 1-9.
Pan et al., "Bidirectional Association Between Depression and Metabolic Syndrome: A Systematic Review and Metaanalysis of Epidemiological Studies". Diabetes Care; 2012, 35(5): 1171-1180.
Russu et al., "Pharmacokinetic-Pharmacodynamic Characterization of Relapse Risk for Paliperidone Palmitate 1-Month and 3-Month Formulations". Journal of Clinical Psychopharmacology 39:567-574, Nov./Dec. 2019.
Samtani, et al.: "Dosing and Switching Strategies for Paliperidone Palmitate", CNS Drugs, 25, 2011, 829-845.
Shymko et al., (2020) Weight Gain and Metabolic Screening in Young People with Early Psychosis on Long Acting Injectable Antipsychotic Medication (Aripiprazole vs Paliperidone). Eady Intervention in Psychiatry; 1-7 DOI: 10.1111/eip.13013.
Trevicta, European Medicines Agency, Apr. 1, 2016, Assessment Report, 49 pages.
Weiden, et al: "Does Half-Life Matter After Antipsychotic Discontinuation? A Relapse Comparison in Schizophrenia with 3 Different Formulations of Paliperidone", Journal of Clinical Psychiatry, Jul./Aug. 2017, 8(7):e813-e820.
Weiden, et al.: "Partial Compliance and Risk of Rehospitalization Among California Medicaid Patients With Schizophrenia", Aug. 2004, vol. 55, No. 8, 886-891.
Fernandez-Miranda et al., Int. Clin. Psycholpharmacol., 2017, 32(1), 6-12, abstract only.
Annex 1, Summary of Product Characteristics, Trevicta (2016), pp. 1-57.
Berwaerts, J., et al., Efficacy and Safety of Paliperidone Palmitate 3-month Formulation in Schizophrenia: a Randomized, Double-blind, Placebo controlled Study. Schizophrenia Bulletin, Mar. 1, 2015, 41, 302.
Clinical trial NCT01515423 entitled "A Randomized, Multicenter, Double Blind, Non-inferiority Study of Paliperidone Palmitate 3 Month and 1 Month Formulations for the Treatment of Subjects With Schizophrenia" (v40 19.02.2015).
ClinicalTrials.Gov., "NCT01515423: Study of Paliperidone Palmitate 3 Month and 1 Month Formulations for the Treatment of Patients with Schizophrenia,", Mar. 11, 2014, (v.36).
FDA approved full prescribing information of Invega Trinza TM Reference ID: 3755541 (rev. May 2015).
Invega Sustenna® (paliperidone palmitate) extended-release injectable suspension, for intramuscular use Initial U.S. Approval, Reference ID 3657038, Nov. 1, 2014, pp. 1-56; Revised Nov. 2014.
Samtani et al., "Dosing and Switching Strategies for Paliperidone Palmitate Based on Population Pharmacokinetic Modelling and Clinical Trial Data" CNS Drugs, vol. 25, Oct. 1, 2011, 829-845 [including Supplementary Digital Content CPNP 2009 Poster Abstracts, Journal of Pharmacy Practice, vol. 22(2), p. 203-268 (2009); Erratum 423].
Samtani, M.N., "Management of antipsychotic treatment discontinuation and interruptions using model-based simulations," Clinical Pharmacology: Advances and Applications, vol. 4, No. 1, Jul. 16, 2012, pp. 25-40.
Samtani, M.N., et al., "Expansion of guidance for the day 8 initiation dose of paliperidone palmitate to avoid a missed dose," Neuropsvchiatric Disease and treatment, vol. 9, May 20, 2013, pp. 721-730.
Stringer, J.L., "Pharmacokinetics," in Basic Concepts in Pharmacology. What you need to know for each drug class, Chaper 4, Fourth Edition, McGraw-Hill Medical, 2011, pp. 16-23.
Sunil, S.J., et al., "Basic Pharmacokinetics", Second Edition, Pharmaceutical Press, published 2012, Introductory pages and p. 41.

DOSING REGIMENS ASSOCIATED WITH EXTENDED RELEASE PALIPERIDONE INJECTABLE FORMULATIONS

CROSS-REFERENCE TO RELATED APPLICATIONS

This application claims the benefit of U.S. Provisional Patent Application No. 63/119,382, filed Nov. 30, 2020, the disclosure of which is incorporated by reference herein.

FIELD OF THE INVENTION

This invention relates to methods of treating a psychiatric patient in need of treatment with long acting injectable paliperidone palmitate formulations.

BACKGROUND OF THE INVENTION

Antipsychotic medications are the mainstay in the treatment of schizophrenia, schizoaffective disorder, and schizophreniform disorders. Antipsychotics were first introduced in the mid-1950s. These typical or first generational drugs are usually effective in controlling the positive symptoms of schizophrenia but are less effective in moderating the negative symptoms or the cognitive impairment associated with the disease. Atypical antipsychotics or second generation drugs, typified by risperidone and olanzapine, were developed in the 1990s, and are generally characterized by effectiveness against both the positive and negative symptoms associated with schizophrenia.

Paliperidone palmitate is the palmitate ester of paliperidone (9-hydroxy-risperidone), a monoaminergic antagonist that exhibits the characteristic dopamine $D_2$ and serotonin (5-hydroxytryptamine type 2A) antagonism of the second generation, atypical antipsychotic drugs. Paliperidone (9-OH risperidone) is the major active metabolite of risperidone. Extended release (ER) osmotic controlled release oral delivery (OROS) paliperidone, as a tablet formulation, is marketed in the United States (U.S.) for the treatment of schizophrenia and maintenance of effect.

Paliperidone palmitate has been developed as a long-acting, intramuscular (i.m.), injectable aqueous nanosuspension for the treatment of schizophrenia and other related diseases that are normally treated with antipsychotic medications. Because of extreme low water solubility, paliperidone esters such as paliperidone palmitate dissolve slowly after an intramuscular injection before being hydrolyzed to paliperidone and made available in the systemic circulation.

Many patients with mental illnesses achieve symptom stability with available oral antipsychotic medications; however, it is estimated that up to 75% have difficulty adhering to a daily oral treatment regimen, i.e. adherence problems. Problems with adherence often result in worsening of symptoms, suboptimal treatment response, frequent relapses and re-hospitalizations, and an inability to benefit from rehabilitative and psychosocial therapies. Once monthly Paliperidone palmitate injection has been developed to provide sustained plasma concentrations of paliperidone, which may greatly enhance compliance with dosing. Paliperidone palmitate formulated as an aqueous nanosuspension is described in U.S. Pat. Nos. 6,077,843 and 6,555,544, each of which is incorporated herein by reference. In addition, dosing regimens of paliperidone palmitate for treating patients is disclosed in U.S. Pat. Nos. 9,439,906 and 10,143, 693, each of which is incorporated herein by reference.

Paliperidone palmitate is an atypical antipsychotic drug administered by intramuscular injection. The original formulation of paliperidone palmitate was a once-monthly antipsychotic and was approved for the treatment of schizophrenia in adults in numerous countries. The acute and sustained efficacy and tolerability profile of once-monthly paliperidone palmitate has been demonstrated in clinical studies totaling more than 3800 patients. Continued treatment with once-monthly paliperidone palmitate in patients who initially responded to it for acute worsening of symptoms resulted in a nearly 4-fold reduction in relapse risk compared with patients randomized to placebo. A later developed three-month formulation offers a substantially longer dosing interval: injections are administered once every three months. This extended dosing interval offers the prospect of fewer opportunities for nonadherence than previously available long acting injectable formulations, thus reducing relapse risk as a result of subtherapeutic plasma concentration and its associated negative consequences in patients with schizophrenia.

Paliperidone is currently available for therapeutic use in 3 formulations; an oral extended-release formulation (INVEGA® Extended Release [ER] tablets; also termed INVEGA® prolonged-release [PR] tablets), and two long-acting injectable (LAI) formulations (paliperidone palmitate one-month injection [INVEGA SUSTENNA® or XEPLION®] and paliperidone palmitate three-month injection [INVEGA TRINZA® or TREVICTA®]). As disclosed herein, another paliperidone palmitate product intended for administration once every six months (paliperidone palmitate six-month injection), with a view to further improving adherence and convenience, is being developed.

Patients who do not regularly take their medications can suffer many consequences, most notably schizophrenia relapse. For oral antipsychotics, medication gaps of as little as one day can double the risk for re-hospitalization. This typically results in worsening of psychiatric comorbidities, loss of employment, interruption of education and impairment of family relationships. The biological consequences include loss of synaptic plasticity of neurons, especially in the frontal lobes. Functionally schizophrenia relapse has been linked to pruning at the level of synaptic neuronal junctions. Overall, this can be radiologically measured by widespread shrinkage of the grey matter of the brain, with accompanying enlargement of the cerebral ventricles. These changes are visible on CT/MRI scanning of the brain. With each successive relapse, further progressive changes to the brain are typically observed. Currently there is no known cure for schizophrenia, and the only proven method to treat the disease is with long-term administration of antipsychotic medications along with social and behavioral interventions. The strongest predictor of schizophrenia relapse is adherence to antipsychotic medications.

A paliperidone palmitate product that is intended to be given once every six months presents a challenge in terms of a patient remembering to come in for treatment at exactly the six-month time point. This is further compounded by the fact that the length of a month varies between 28-31 days. Because an injection is intended to be given by a health care professional, and not self-administered, allowing patients to have flexibility to schedule their visit to the clinic and receive their injection is an important consideration. Most other antipsychotic regimens (oral and LAI) are typically given over a one-month cycle, and patients return to a clinic to either get a refill of their prescription or an injection. A six-month dosing interval presents a unique challenge to ensure compliance.

Patients also at times miss their doses of medication. Consequently, there is a need to re-initiate a dosing regimen for patients who miss their regularly scheduled dose of medication.

Moreover, weight gain is a very common phenomenon in the treatment of patients requiring antipsychotic medication. During long-term treatment with antipsychotic drugs in patients with schizophrenia or schizoaffective or any other psychotic disorder, obesity and other cardiovascular risk factors increase and mostly negatively impact patients long-term morbidity and even mortality. Patients with severe mental disorders also face stigmatization and a reduced quality of life due to treatment side-effects like weight gain, especially young patients in early stages of their illness. Avoiding or stabilizing weight gain can help those patients maintain their social life, reduce stigma, and increase quality-of-life. Any potential for a decrease of body weight or a stabilization of current weight would be a benefit for patients treated with risperidone or paliperidone who are in need of long-term symptom protection.

SUMMARY OF THE INVENTION

In one embodiment, the present disclosure provides methods for administering paliperidone palmitate to a patient in need thereof who has been administered a first dose of a paliperidone palmitate extended-release injectable suspension, comprising administering a second dose of the paliperidone palmitate extended-release injectable suspension to a deltoid or gluteal muscle of the patient up to two weeks before or three weeks after a time that is six months after administration of the first dose, without an intervening dose of paliperidone palmitate between the first dose and the second dose.

In other embodiments, the disclosure provides re-initiation dosing regimens for patients who miss their regularly scheduled dose of medication, with the regimen depending on the time elapsed from the patient's last dose. For example, the disclosure provides methods for administering paliperidone palmitate to a patient in need thereof who has been administered a first dose of a first paliperidone palmitate extended-release injectable suspension (first suspension), comprising administering in a deltoid muscle of the patient a re-initiation loading dose of a second paliperidone palmitate extended-release injectable suspension (second suspension) at a time that is more than six months and three weeks after administration of the first dose of the first suspension but less than eight months after administration of said first dose of the first suspension; and administering in a deltoid or gluteal muscle of the patient a maintenance dose of the first suspension at a time that is about one month (±7 days) after administering the re-initiation loading dose of the second suspension.

Other re-initiation regimens include administering paliperidone palmitate to a patient in need thereof who has been administered a first dose of a first paliperidone palmitate extended-release injectable suspension (first suspension) wherein such administration involves administering to a deltoid muscle of the patient a first re-initiation loading dose of 156 mg paliperidone palmitate of a second paliperidone palmitate extended-release injectable suspension (second suspension) at a time that is from eight months up to and including eleven months after administration of the first dose of the first suspension; administering in a deltoid muscle of the patient a second re-initiation loading dose of 156 mg paliperidone palmitate of the second suspension on about day 8 (±4 days) after administering the first re-initiation loading dose of the second suspension; and administering in a deltoid or gluteal muscle of the patient from about 1092 mg to about 1560 mg paliperidone palmitate of a maintenance dose of the first suspension about one month (±7 days) after administering the second re-initiation loading dose of the second suspension.

Other re-initiation regimens include administering paliperidone palmitate to a patient in need thereof who has been administered a first dose of a first paliperidone palmitate extended-release injectable suspension (first suspension), wherein such administration involves (1) administering in a deltoid muscle of the patient a first re-initiation loading dose of 234 mg of paliperidone palmitate of a second paliperidone palmitate extended-release injectable suspension (second suspension) at a time that is more than eleven months after administration of the first dose of the first suspension; (2) administering in a deltoid muscle of the patient a second re-initiation loading dose of 156 mg of paliperidone palmitate of the second suspension on about day 8 (±4 days) after administering the first re-initiation loading dose of the second suspension; (3) administering in a deltoid or gluteal muscle of the patient a first re-initiation maintenance dose of 39 mg to about 234 mg of paliperidone palmitate of the second suspension about one month (+7 days) after administering the second re-initiation loading dose; (4) administering in a deltoid or gluteal muscle of the patient a second re-initiation maintenance dose of from about 39 mg to about 234 mg of paliperidone palmitate of the second suspension about one month (±7 days) after administering the first re-initiation maintenance dose of second suspension; (5) administering in a deltoid or gluteal muscle of the patient a third re-initiation maintenance dose of from about 39 mg to about 234 mg of paliperidone palmitate of the second suspension about one month (±7 days) after administering the second re-initiation maintenance dose of the second suspension, and (6) administering in a deltoid or gluteal muscle of the patient from about 1092 mg to about 1560 mg of paliperidone palmitate of a maintenance dose of the first suspension about one month (±7 days) after administering the third re-initiation maintenance dose of the second suspension. Additional re-initiation maintenance doses may be administered before the maintenance dose of the first suspension (e.g. a fourth re-initiation maintenance dose, fifth re-initiation maintenance dose, etc.). In certain embodiments, the re-initiation maintenance doses of paliperidone palmitate are from about 156 to about 234 mg.

The disclosure also provides methods of stabilizing or decreasing body weight of a patient who has been treated with a paliperidone palmitate extended-release injectable suspension at either one-month intervals (PP1M) or three-month intervals (PP3M), comprising administering a last dose of the PPIM or the PP3M and then administering an initial dose of a paliperidone palmitate extended-release injectable suspension having a six month dosing interval (PP6M).

DETAILED DESCRIPTION

Figure 1:
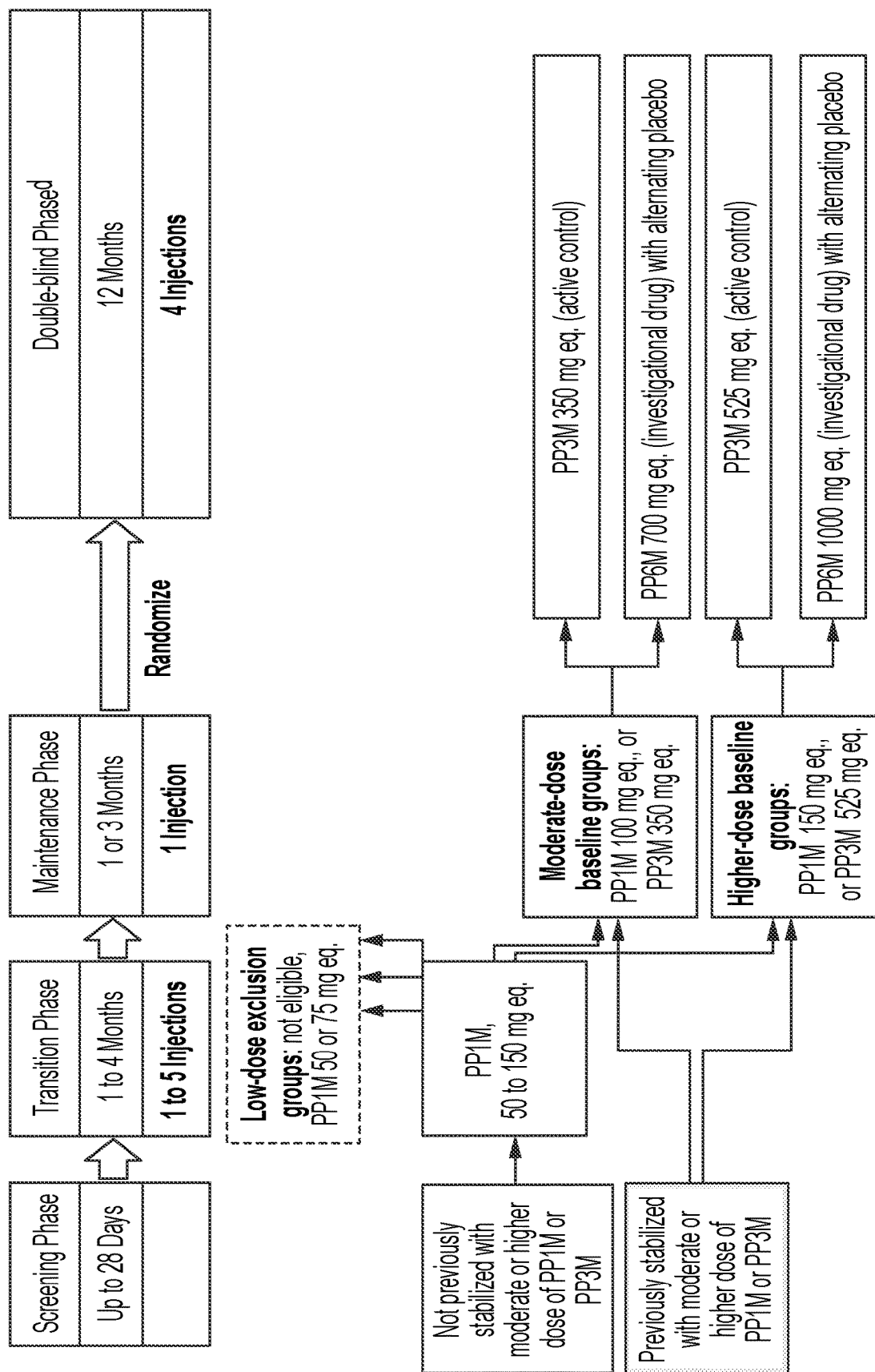
FIG. 1 depicts a flow chart of a double-blind, randomized, active-controlled, parallel-group study of paliperidone palmitate six-month formulation.

The presently disclosed inventive subject matter may be understood more readily by reference to the following detailed description taken in connection with the accompanying examples, which form a part of this disclosure. It is to be understood that these inventions are not limited to the specific formulations, methods, or parameters described and/or shown herein, and that the terminology used herein is for the purpose of describing particular embodiments by way of example only and is not intended to be limiting of the claimed inventions.

When a value is expressed as an approximation by use of the descriptor "about" or "substantially" it will be understood that the particular value forms another embodiment. In general, use of the term "about" or"substantially" indicates approximations that can vary depending on the desired properties sought to be obtained by the disclosed subject matter and is to be interpreted in the specific context in which it is used, based on its function.

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiments and such a combination is considered to be another embodiment. Conversely, various features of the invention that are, for brevity, described in the context of a single embodiment, may also be provided separately or in any sub-combination.

Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded, thus, a recitation of "1 to 5" may support "1 and 3-5, but not 2", or simply "wherein 2 is not included."

As used herein, "PP1M" refers to a paliperidone palmitate extended-release injectable suspension or other type of formulation having an amount of paliperidone palmitate suitable for a dosing interval of about one-month. A commercially available example includes INVEGA SUSTENNA® or XEPLION®. See also U.S. Pat. No. 9,439,906 incorporated herein by reference.

As used herein, "PP3M" refers to a paliperidone palmitate extended-release injectable suspension or other type of formulation having an amount of paliperidone palmitate suitable for a dosing interval of about three-months. A commercially available example includes INVEGA TRINZA® or TREVICTA®. See also U.S. Pat. No. 10,143,693 incorporated herein by reference.

As used herein, "PP6M" refers to a paliperidone palmitate extended-release injectable suspension or other type of formulation having an amount of paliperidone palmitate suitable for a dosing interval of about six-months.

Paliperidone is effective for the treatment of psychosis and has been used to treat schizophrenia and schizoaffective disorders. Accordingly, PP6M is suitable for the treatment of psychotic disorders including but not limited to schizophrenia and/or schizoaffective disorder or bipolar disorder.

PP6M is typically administered to patients who have been adequately treated with PP1M (e.g. INVEGA SUSTENNA®) for several months, and, in certain embodiments, for at least four months, with PP1M doses of about 156 mg or about 234 mg paliperidone palmitate. It is further preferred that the last two doses of PP1M are at the same dosage strength before starting PP6M. Alternatively, PP6M is administered to patients who have been adequately treated with PP3M (e.g. INVEGA TRINZA®) for at least one three-month cycle, with PP3M doses of about 546 mg or about 819 mg paliperidone palmitate.

PP6M will typically be provided with a dose in the range of from about 1000 mg to about 1600 mg of paliperidone palmitate to provide a sustained therapeutic concentration of paliperidone over the six-month dosing interval. Preferably, the PP6M is provided in dose strengths of about 1092 mg or about 1560 mg paliperidone palmitate. The drug product hydrolyzes to the active moiety, paliperidone, resulting in dose strengths of about 700 mg eq. or 1000 mg eq. of paliperidone, respectively.

PP6M is preferably provided in a prefilled syringe (cyclic-olefin-copolymer) prefilled with either 700 mg eq. (3.5 mL) or 1000 mg eq. (5.0 mL) paliperidone (as 1092 mg or 1560 mg paliperidone palmitate, respectively) with a plunger stopper, a plunger rod, and tip cap (bromobutyl rubber), a backstop, and a needle, preferably a thin walled 20 gauge (G), 1½-inch safety needle.

PP6M is intended for intramuscular use. It is not recommended to administer by any other route. Care should be taken to avoid inadvertent injection into a blood vessel. Doses are preferably administered in a single injection; for example, divided injections could change the release profile. It is otherwise preferred that injections be administered slowly, deep into the muscle of the patient, in particular, the deltoid or gluteal muscle. Typically, PP6M is administered to the gluteal muscle given the volume of the injection.

Intramuscular Injection

Typically, regardless of the patient's weight, PP6M is administered intramuscularly using a thin walled syringe, for example, a 20 gauge (G), 1½-inch needle in the deltoid muscle or the gluteal muscle. To the extent administered to the deltoid muscle, paliperidone palmitate is typically administered into the center of the deltoid muscle, preferably alternating between the two deltoid muscles per single injection (i.e. the opposite deltoid muscle is used at the next scheduled dosing interval). For PP6M, gluteal intramuscular administration is preferred. For example, PP6M may be administered into the upper-outer quadrant of the gluteal muscle. It is also preferred that gluteal injections should be alternated between the two gluteal muscles per single injection (i.e. the opposite gluteal muscle is used at the next scheduled dosing interval).

Incomplete Administration

PP6M is typically a highly concentrated product. As a result, an important consideration is to ensure complete suspension/resuspension of the product before administration. To avoid an incomplete administration, the syringe is shaken and/or mechanically agitated to obtain a uniform dispersion of the suspension. For example, the syringe is preferably shaken fast with the syringe tip cap pointing up for at least 15 seconds. A brief rest may be taken, and then the syringe may be, and preferably is, shaken again for another 15 seconds. The injection is then preferably done immediately or within 5 minutes of the last shaking to ensure resuspension and that the needle does not get clogged during injection.

Due to the slow release characteristics of PP6M, the product is not intended to be used in patients who are immediately transitioning from oral to LAI antipsychotic therapy. Rather, PP6M is intended to be used in patients who are adequately treated with either PP1M or PP3M at the time of initiation of PP6M. The determination of adequately treated is typically up to the judgment of the prescribing clinician. Typically, PP6M dosing is initiated: A) one month after being adequately treated with PPIM (e.g. INVEGA SUSTENNA®) for at least four months; or B) three months after a PP3M (e.g. INVEGA TRINZA®) dose has been established as adequate treatment. PP6M may be administered one month (±7 days) after a last PPIM injection, or three months (+14 days) after a last PP3M injection.

Following the initial PP6M injection, PP6M should be administered every six months. If needed, dose adjustment can be made every six months in increments within the range of 1092 mg to 1560 mg paliperidone palmitate based on individual patient tolerability and/or efficacy. Typically, the dosage is adjusted to about 1092 mg or to about 1560 mg paliperidone palmitate. Due to the long-acting nature of PP6M, the patient's response to an adjusted dose may not be apparent for several months.

Dosing Window

As noted herein, nonadherence is a major issue in the treatment of psychiatric patients, especially those with schizophrenia, who often abruptly discontinue medication without consulting their practitioner or caregiver. Lack of adherence has been identified as the strongest predictor of relapse, which typically results in worsening of psychiatric comorbidities, loss of employment, interruption of education and impairment of family relationships. For oral antipsychotics, medication gaps of as little as one day can double the risk for re-hospitalization. Long acting injectable (LAI) antipsychotics were developed to address this problem and to ensure timely interventions for non-adherent patients to prevent relapse and hospitalization.

The commonly encountered difficulty in clinical practice, however, is that subjects need to return to the clinic on a specific date after receiving their previous maintenance injection of a LAI antipsychotic. Having a window in which injections could be given would give greater flexibility to prescribers, patients, and caregivers. This window will often be prescribed by a medical professional and/or set by a regulatory agency.

Previously, a dosing window of ±1 week around the target injection date (scheduled injection date based on dosing interval) was established for PPIM. For PP3M, this window was expanded to ±2 weeks around the target injection date. It has now been found that a dosing window of up to 2 weeks earlier and up to 3 weeks after the target injection date for PP6M may be used, offering further dosing flexibility.

Dosing recommendations have historically been aimed at paliperidone plasma concentrations above a threshold of 7.5 ng/mL. This threshold has been associated with a central Dopamine type 2 (D2) receptor occupancy of 60% while receptor occupancy in the range of 60%-80% is considered necessary for a satisfactory antipsychotic response. As reflected in the example section (see Example 7), simulations were conducted to evaluate the relationship between median time to relapse and the point at which the median paliperidone concentration goes under 7.5 ng/mL. An apparent delay lasting from several weeks to several months was observed between the time point when median plasma paliperidone concentration decreased to 7.5 ng/mL and the median time to relapse, i.e., the time point when half of the subjects had experienced relapse, while the other half of the subjects either relapsed later or did not relapse during the study. Thus, it appears that the therapeutic effect is more prolonged than the expected effect based on the 7.5 ng/mL threshold, and the relapse protection window may be extended farther in the positive direction.

In one embodiment, a dosing window of up to 2 weeks earlier and up to 3 weeks after the target injection date for PP6M (i.e. the scheduled six-month time point) is used. Accordingly, the disclosure includes methods for administering paliperidone palmitate to a patient in need thereof who has been administered a first dose of a paliperidone palmitate extended-release injectable suspension, comprising administering a second dose of the paliperidone palmitate extended-release injectable suspension to a deltoid or gluteal muscle, preferably the gluteal muscle, of the patient up to two weeks before or three weeks after a time that is six months after administration of the first dose, without an intervening dose of paliperidone palmitate between the first dose and the second dose. It should be recognized that the first dose and the second dose are doses within the sequence of the described methods, but do not necessarily refer to the very first (initial) or second dose administered to the patient.

Unless otherwise indicated, as used herein, a "month" refers to a Gregorian calendar month and may vary from as little as 28 days (e.g., February) to 31 days (e.g., October), e.g., 28, 29, 30, or 31 days. The six-month time point reflects six consecutive calendar months. As indicated herein, certain testing reflected in the examples, including simulations, were based on 30 days being used for a month. A "week" refers to seven days.

In some embodiments, other dosing windows may be considered. For example, a dosing window of up to one week earlier and up to two weeks after, or up to one week earlier and up to three weeks after, or up to two weeks earlier and up to two weeks after, the target injection date for PP6M. In still other embodiments, the second dose is administered up to four weeks, or up to five weeks after a time that is six months after administration of the first dose as part of a dosing window. Any combination of these time periods before and after a time that is six months after administration of the first dose may be utilized. In certain embodiments, the dosing window is applied to patients that have reached a steady-state paliperidone plasma concentration.

The first dose and second dose, independently, are typically from about 1000 mg to about 1600 mg of paliperidone palmitate. In particular, the first dose and second dose, independently, are about 1092 mg or about 1560 mg paliperidone palmitate. In other embodiments, the first dose and the second dose are each about 1092 mg paliperidone palmitate. In another embodiment, the first dose and second dose are each about 1560 mg paliperidone palmitate.

Typically, the plasma concentration of paliperidone in the patient is about 5 to about 50 ng/mL at the time of the second dose, or about 10 to about 40 ng/mL at the time of the second dose. For example, when the first dose is 1092 mg paliperidone palmitate, the plasma concentration of paliperidone in the patient is about 5 to about 30 ng/mL, or about 10 to about 25 ng/mL, at the time of the second dose. When the first dose is 1560 mg paliperidone palmitate, the plasma concentration of paliperidone in the patient is about 9 to about 40 ng/mL, or about 20 to about 30 ng/mL, at the time of the second dose. In this context, "at the time of the second dose" refers to concentration levels immediately preceding the second dose, typically representing $C_{trough}$ values.

In other aspects, the plasma concentration of paliperidone in the patient achieves a peak of about 10 to about 150 ng/mL after administration of the second dose, or about 35 ng/mL to about 125 ng/mL after administration of the second dose. For example, when the first dose is 1092 mg paliperidone palmitate, the plasma concentration of paliperidone in the patient achieves a peak of about 10 to about 125 ng/mL, or about 50 to about 90 ng/mL, after administration of the second dose. When the first dose is 1560 mg paliperidone palmitate, the plasma concentration of paliperidone in the patient achieves a peak of about 35 to about 145 ng/mL, or about 70 to about 110 ng/mL, after administration of the second dose.

In certain embodiments, PP3M and PP6M can have the same formulation. In such an embodiment, the pharmacokinetic properties of PP6M will be similar to PP3M, but such a PP6M would be expected to have higher peaks and lower troughs given the higher amount of drug and longer frequency of administration. As shown in Example 6, the absolute drug plasma concentrations were lower for PP6M at its target interval vs. PP3M at its target interval. Given that PP3M had established a dosing window of ±2 weeks around the target injection date, expanding the dosing window in the positive direction for a formulation that results in lower drug plasma concentrations at the target interval point would not have been suggested. But, as reflected herein, it was discovered that the therapeutic effect is more prolonged than the expected effect based on pharmacokinetic data, thus allowing the dosing window to extend farther in the positive direction.

Missed Doses

Patients who receive LAI antipsychotics routinely return to their health care provider to receive injections of their medication. The timing of their dose is typically carefully prescribed. As noted herein, for any given antipsychotic an optimal dosing cycle is recommended, along with a dosing window (±) in which they can receive their medication without any untoward side effects or loss of efficacy. In the present disclosure, following an initial dose of PP6M, PP6M should be administered every six months. Missed doses of PP6M should be avoided, although injections given within the prescribed dosing window would not be considered a missed dose. If needed, dose adjustment can be made every six months between the dose levels of 1092 mg to 1560 mg paliperidone palmitate based on individual patient tolerability and/or efficacy.

However, despite this, it is a frequent occurrence for schizophrenia patients to become noncompliant at some point during their illness. Therefore, based on population pharmacokinetic simulations, guidelines are provided in the event of missed doses of PP6M beyond the dosing-window.

The present disclosure provides a mechanism by which patients can resume treatment with PP6M in case they become fully or partially non-adherent. Since dosing of PP6M is dependent on a patient first being stabilized on PP1M/PP3M, this would reduce the necessity of patients having to start de-novo. In addition, because it was discovered that the therapeutic effect is more prolonged than the expected effect based on pharmacokinetic data, patients that had at least one PP6M injection are expected to be relapse-free for a longer period of time. This provides a positive effect of PP6M on preventing relapse, even in situations of non-adherence.

The disclosure provides re-initiation dosing regimens for patients who miss their regularly scheduled dose of medication, i.e., are outside the prescribed dosing window, with the regimen depending on the time elapsed from the patient's last dose. In some embodiments, the missed dose is over six months and three weeks, but less than seven to nine months, e.g. less than eight months, after the last injection.

For example, to the extent the dosing window is up to 2 weeks earlier and up to 3 weeks after the target injection date, the disclosure provides a method for administering paliperidone palmitate to a patient in need thereof who has been administered a first dose of a first paliperidone palmitate extended-release injectable suspension (first suspension), comprising administering in a deltoid muscle of the patient a re-initiation loading dose of a second paliperidone palmitate extended-release injectable suspension (second suspension) at a time that is more than six months and three weeks after administration of the first dose of the first suspension but less than seven to nine months, e.g. less than eight months, after administration of said first dose of the first suspension; and administering in a deltoid or gluteal muscle of the patient a maintenance dose of the first suspension at a time that is about one month (±7 days) after administering the re-initiation loading dose of the second suspension. In one embodiment, the re-initiation loading dose of the second suspension and the maintenance dose of the first suspension are selected based on the first dose of the first suspension as shown below in Table 1, with the administration of the first suspension preferably in the gluteal muscle of the patient.

TABLE 1

| First dose of first suspension | Re-initiation loading dose of second suspension | Maintenance dose of first suspension |
|---|---|---|
| 1092 mg | 156 mg | 1092 mg |
| 1560 mg | 234 mg | 1560 mg |

To the extent a different dosing window is prescribed, the same re-initiation dosing regimen noted above may be implemented but adjusted based on the outer dosing window parameter. For example, if the dosing window was up to 1 week earlier and up to 2 weeks after the target injection date, the re-initiation loading dose of the second suspension would be administered at a time that is more than six months and two weeks after administration of the first dose of the first suspension but less than seven to nine months, e.g. less than eight months, after administration of said first dose of the first suspension.

Other re-initiation regimens are based on a missed dose of seven to nine months and up to and including ten to fourteen months after the last injection. For example, the disclosure includes administering paliperidone palmitate to a patient in need thereof who has been administered a first dose of a first paliperidone palmitate extended-release injectable suspension (first suspension), comprising administering to a deltoid muscle of the patient a first re-initiation loading dose of 156 mg paliperidone palmitate of a second paliperidone palmitate extended-release injectable suspension (second suspension) at a time that is from seven to nine months, e.g. from eight months, up to and including ten to fourteen months, e.g. up to and including eleven months, after administration of the first dose of the first suspension; administering in a deltoid muscle of the patient a second re-initiation loading dose of 156 mg paliperidone palmitate of the second suspension on about day 8 (±4 days) after administering the first re-initiation loading dose of the second suspension, and administering in a deltoid or gluteal muscle of the patient from about 1092 mg to about 1560 mg paliperidone palmitate of a maintenance dose of the first suspension about one month (±7 days) after administering the second re-initiation loading dose of the second suspension. In one embodiment, the first dose of the first suspension is about 1092 mg paliperidone palmitate and the maintenance dose of the first suspension is about 1092 mg paliperidone palmitate. In another embodiment, the first dose of the first suspension is about 1560 mg paliperidone palmitate and the maintenance dose of the first suspension is about 1560 mg paliperidone palmitate. In preferred embodiments, the administration of the first suspension is in the gluteal muscle of the patient.

Other re-initiation regimens are based on a missed dose of more than ten to fourteen months after the last injection. For example, the disclosure includes administering paliperidone palmitate to a patient in need thereof who has been administered a first dose of a first paliperidone palmitate extended-release injectable suspension (first suspension), comprising (1) administering in a deltoid muscle of the patient a first re-initiation loading dose of 234 mg paliperidone palmitate of a second paliperidone palmitate extended-release injectable suspension (second suspension) at a time that is more than ten to fourteen months, e.g. more than eleven months, after administration of the first dose of the first suspension; (2) administering in a deltoid muscle of the patient a second re-initiation loading dose of 156 mg paliperidone palmitate of the second suspension on about day 8 (±4 days) after administering the first re-initiation loading dose of the second suspension; (3) administering in a deltoid or gluteal muscle of the patient a first re-initiation maintenance dose of 39 mg to about 234 mg paliperidone palmitate of the second suspension about one month (±7 days) after administering the second re-initiation loading dose; (4) administering in a deltoid or gluteal muscle of the patient a second re-initiation maintenance dose of from about 39 mg to about 234 mg paliperidone palmitate of the second suspension about one month (±7 days) after administering the first re-initiation maintenance dose of the second suspension: (5) administering in a deltoid or gluteal muscle of the patient a third re-initiation maintenance dose of from about 39 mg to about 234 mg paliperidone palmitate of the second suspension about one month (±7 days) after administering the second re-initiation maintenance dose of the second suspension; and (6) administering in a deltoid or gluteal muscle of the patient from about 1092 mg to about 1560 mg paliperidone palmitate of a maintenance dose of the first suspension about one month (±7 days) after administering the third re-initiation maintenance dose of the second suspension. Preferably, the first suspension is administered in the gluteal muscle. In one embodiment, the first dose of the first suspension is about 1092 mg paliperidone palmitate and the maintenance dose of the first suspension is about 1092 mg paliperidone palmitate. In another embodiment, the first dose of the first suspension is about 1560 mg paliperidone palmitate and the maintenance dose of the first suspension is about 1560 mg paliperidone palmitate. In other embodiments, the second and third re-initiation maintenance doses of second suspension are the same. Additional re-initiation maintenance doses may be administered in one-month (±7 days) intervals before the maintenance dose of the first suspension (e.g. a fourth re-initiation maintenance dose, a fifth re-initiation maintenance dose, etc.). In certain embodiments, the re-initiation maintenance doses of paliperidone palmitate are from about 156 to about 234 mg. With respect to any of the re-initiation regimens, following the maintenance dose of the first suspension, the first suspension is typically administered in six-month intervals as noted herein.

In particular embodiments, the first suspension is PP6M and the second suspension is PP1M. Exemplary re-initiation regimens based on PP1M and PP6M are further disclosed in Example 8. A goal of a re-initiation regimen is to achieve a quick return to paliperidone plasma concentrations as before the missed dose without creating an overshoot due to the applied re-initiation regimen. It should be recognized that the methods do not contemplate intervening doses of paliperidone palmitate between the enumerated doses of the missed dosing regimens described herein, e.g., between the first dose and the re-initiation loading dose.

Another aspect of the present disclosure is an observed effect for longer acting paliperidone palmitate treatments on stabilizing or decreasing weight in a patient population for which most treatments cause weight gain. In particular, it has been found that transitioning patients who have been adequately treated with PP1M or PP3M to PP6M can reduce, stop, or potentially partially reverse a paliperidone-induced weight gain while maintaining good pharmacological efficacy and maintaining relapse prevention.

As a result, the present disclosure fulfills an unmet medical need for overweight patients treated with risperidone or paliperidone who are in need of long-term symptom protection and therefore antipsychotic treatment but for whom a continuous weight increase is not acceptable. Increasing weight during long-term treatment has metabolic effects which increase risk factors for higher morbidity and mortality (e.g. due to cardiovascular disease). In addition, increasing weight can impact patients mobility and functionality and reduce quality of life significantly. The PP6M formulation and regimen disclosed herein allows a weight neutral or weight reducing treatment for patients while providing the same efficacy compared to other paliperidone or paliperidone palmitate formulations (e.g. PP1M or PP3M).

In one embodiment, the disclosure provides methods of stabilizing or decreasing body weight of a patient who has been treated with a paliperidone palmitate extended-release injectable suspension at either one-month intervals (PP1M) or three-month intervals (PP3M), comprising administering a last dose of the PP1M or the PP3M and then administering an initial dose of a paliperidone palmitate extended-release injectable suspension having a six month dosing interval (PP6M). In certain embodiments, the patient has been treated with the PP1M for at least four months, at least five months, or at least six months. In other embodiments, the patient has been treated with the PP3M for at least one 3-month interval, at least two 3-month intervals, or at least three 3-month intervals.

In embodiments where the patient has been treated with PP1M, the initial dose of PP6M is administered about one month (±7 days) after the last dose of the PP1M is administered. Typically, when the last dose of the PP1M is about 156 mg paliperidone palmitate, the initial dose of PP6M is about 1092 mg paliperidone palmitate. In other embodiments, when the last dose of the PP1M is about 234 mg paliperidone palmitate, the initial dose of PP6M is about 1560 mg paliperidone palmitate.

In embodiments where the patient has been treated with PP3M, the initial dose of PP6M is administered about three months (±4 days) after the last dose of the PPIM is administered. Typically, when the last dose of the PP3M is about 546 mg paliperidone palmitate, the initial dose of PP6M is about 1092 mg paliperidone palmitate. In other embodiments, when the last dose of the PP3M is about 819 mg paliperidone palmitate, the initial dose of PP6M is about 1560 mg paliperidone palmitate.

Following the initial dose of the PP6M, the PP6M is administered in six-month intervals as noted herein.

Further analysis of the data showed particular benefits in overweight patients (body mass index (BMI) of about 25 and less than about 30) and younger patients (about 18 to about 25 years old).

In certain embodiments, at the time of the last dose of PPIM or PP3M, the patient has a body mass index (BMI) of about 25 to less than about 30.

In other embodiments, at the time of the last dose of PP1M or PP3M, the patient has an age of about 18 years old to about 25 years old.

Typically, weight stabilization refers to a BMI change of about −1 to about +1, or from about −0.5 to about +0.5, from the timepoint of the transition to PP6M (from the time of the initial dose of PP6M). Preferably the BMI change is about zero. With respect to body weight decrease, a negative weight change from the timepoint of the transition to PP6M can be seen as a weight decrease. Such stabilization or weight decrease may occur within about twelve months from the timepoint of the transition to PP6M.

In other aspects, the patient's body weight is assessed or determined at the time of the last dose of the PP1M or PP3M, at the time of the initial dose of PP6M, at subsequent time points following the transition to PP6M, or a combination thereof.

Paliperidone Palmitate Formulations

Paliperidone esters are antipsychotic agents belonging to the chemical class of benzisoxazole derivatives, which contains a racemic mixture of (+)- and (−)-paliperidone, which are described in U.S. Pat. No. 5,254,556 (incorporated herein by reference). The chemical name for paliperidone palmitate is (=)-3-[2-[4-(6-fluoro-1,2-benzisoxazol-3-yl)-1-piperidinyl]ethyl]-6,7,8,9-tetrahydro-2-methyl-4-oxo-4H-pyrido[1,2-c]pyrimidin-9-yl hexadecanoate. The structural formula is:

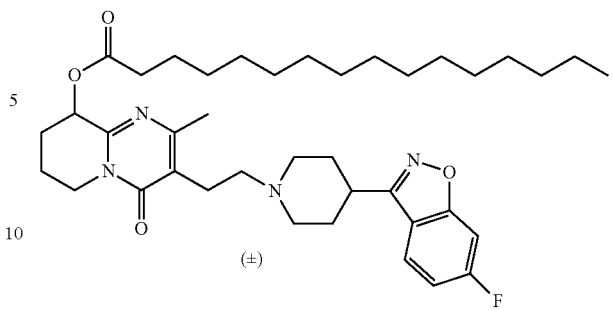

Paliperidone esters may be formulated with pharmaceutical excipients into injectable dosage forms as described in U.S. Pat. Nos. 5,254,556 and 6,077,843 both of which are incorporated herein by reference. Injectable formulations may be formulated in aqueous carriers.

As described in U.S. Pat. No. 9,439,906, incorporated herein by reference, a one-month aqueous formulation is a nano particle suspension wherein the nano particles have average sizes of less than about 2,000 nm to about 100 nm. For example, the nano particles have an average particle size (d50) of from about 1,600 nm to about 400 nm, or from about 1,400 nm to about 900 nm. The d90 is less than about 5,000 nm, or less than about 4,400 nm. The d10 is from about 300 nm to about 600 nm. As used herein, d10: the portion of particles with diameters smaller than this value is 10%; d50: the portion of particles with diameters smaller than this value are 50%; d90: the portion of particles with diameters smaller than this value is 90%; when measured by art-known conventional techniques, such as sedimentation field flow fractionation, photon correlation spectroscopy or disk centrifugation.

In certain embodiments, a three-month (PP3M) formulation has average particle sizes of less than about 20 µm to about 1 µm. In other embodiments, the particles have an average particle size (d50) of from about 5 µm to about 15 µm, from about 3 µm to about 10 µm; or from about 5 µm to about 9 µm. The d90 is about 50 µm; from about 10 µm to about 30 µm; or from about 10 µm to about 20 µm. The d10 is from about 1 µm to about 10 µm, or from about 1 µm to about 5 µm.

In certain embodiments, a six-month (PP6M) formulation has average particle sizes of less than about 30 µm to about 1 µm, or about 20 µm to about 1 µm. In other embodiments, the particles have an average particle size (d50) of from about 3 µm to about 25 µm; from about 5 µm to about 15 pin, from about 3 µm to about 10 µm, or from about 5 µm to about 9 µm. The d90 is 60 µm; or about 50 µm; from about 10 µm to about 30 µm; or from about 10 µm to about 20 µm. The d10 is from about 1 µm to about 15 µm, from about 1 µm to about 10 µm; or from about 1 µm to about 5 µm.

Suitable aqueous nanoparticle formulations are described in U.S. Pat. No. 6,555,544 which is incorporated herein by reference. In some embodiments, the formulation comprises micro particles, a surfactant, a suspending agent, and optionally one or more additional ingredients selected from the group consisting of preservatives, buffers and an isotonizing agent.

Useful surface modifiers for paliperidone palmitate formulations are believed to include those that physically adhere to the surface of the active agent but do not chemically bond thereto. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available TWEENS™, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethylcellulose phtalate, noncrystalline cellulose, magnesium aluminate silicate, triethanolamine, polyvinyl alcohol (PVA), poloxamers, tyloxapol and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone; tyloxapol, poloxamers, such as PLURONIC™ F68, F108 and F127 which are block copolymers of ethylene oxide and propylene oxide available from BASF; poloxamines, such as TETRONIC™ 908 (T908) which is a tetrafunctional block copolymer derived from sequential addition of ethylene oxide and propylene oxide to ethylenediamine available from BASF; dextran; lecithin; Aerosol OT™ (AOT) which is a dioctyl ester of sodium sulfosuccinic acid available from Cytec Industries; DUPONOL™ P which is a sodium lauryl sulfate available from DuPont: TRITON™ X-200 which is an alkyl aryl polyether sulfonate available from Rohm and Haas; TWEEN™ 20, 40, 60 and 80 which are polyoxyethylene sorbitan fatty acid esters available from ICI Specialty Chemicals; SPAN™ 20, 40, 60 and 80 which are sorbitan esters of fatty acids; ARLACEL™ 20, 40, 60 and 80 which are sorbitan esters of fatty acids available from Hercules, Inc.; CARBOWAX™ 3550 and 934 which are polyethylene glycols available from Union Carbide; CRODESTA™ F110 which is a mixture of sucrose stearate and sucrose distearate available from Croda Inc.; CRODESTAT™ SL-40 which is available from Croda, Inc.; hexyldecyl trimethyl ammonium chloride (CTAC); bovine serum albumin and SA90HCO which is $C_{18}H_{17}CH_2(CON(CH_3)CH_2(CHOH)_4CH_2OH)_2$. The surface modifiers which have been found to be particularly useful include tyloxapol and a poloxamer, preferably, Pluronic™ F108 and Pluronic™ F68.

Pluronic™ F108 corresponds to poloxamer 338 and is the polyoxyethylene, polyoxypropylene block copolymer that conforms generally to the formula $HO[CH_2CH_2O]_x[CH(CH_3)CH_2O]_y[CH_2CH_2O]_zH$ in which the average values of x, y and z are respectively 128, 54 and 128 Other commercial names of poloxamer 338 are Hodag NONIONIC™ 1108-F available from Hodag, and SYNPERONIC™ PE/F108 available from ICI Americas.

The optimal relative amount of paliperidone palmitate and the surface modifier depends on various parameters. The optimal amount of the surface modifier can depend, for example, upon the particular surface modifier selected, the critical micelle concentration of the surface modifier if it forms micelles, the surface area of the antipsychotic agent, etc. The specific surface modifier preferably is present in an amount of about 0.1 to about 1 mg per square meter surface area of the paliperidone palmitate. It is preferred in the case of paliperidone palmitate (9-hydroxyrisperidone palmitate) to use PLURONIC™ F108 as a surface modifier, a relative amount (w/w) of both ingredients of approximately 6:1 is preferred.

The particles of this invention can be prepared by a method comprising the steps of dispersing paliperidone palmitate in a liquid dispersion medium and applying mechanical means in the presence of grinding media to reduce the particle size of the antipsychotic agent to an effective average particle size. The particles can be reduced in size in the presence of a surface modifier. Alternatively, the particles can be contacted with a surface modifier after attrition.

A general procedure for preparing the particles described herein includes (a) obtaining paliperidone palmitate; (b) adding the paliperidone palmitate to a liquid medium to form a premix; and (c) subjecting the premix to mechanical means in the presence of a grinding medium to reduce the effective average particle size.

The paliperidone palmitate may be prepared using techniques known in the art. It is preferred that the particle size of the paliperidone palmitate be less than about 100 µm as determined by sieve analysis. If the particle size of the paliperidone palmitate is greater than about 100 µm, then it is preferred that the particles of paliperidone palmitate be reduced in size to less than 100 µm.

The paliperidone palmitate can then be added to a liquid medium in which it is essentially insoluble to form a premix. The concentration of paliperidone palmitate in the liquid medium (weight by weight percentage) can vary widely and depends on the selected surface modifier and other factors. Suitable concentrations of paliperidone palmitate in compositions vary from about 0.1% to about 60%, preferably is from about 0.5% to about 30%, and more preferably, is approximately 7% (w/v). For PP1M, it is currently preferred to use a concentration of about 100 mg eq. of paliperidone per mL or about 156 mg of paliperidone palmitate per mL. For PP3M, it is preferred to use a concentration of about 200 mg eq. of paliperidone per mL or about 312 mg of paliperidone palmitate per mL. For PP6M, it is preferred to use a concentration of about 200 mg eq. of paliperidone per mL or about 312 mg of paliperidone palmitate per mL.

A more preferred procedure involves the addition of a surface modifier to the premix prior to its subjection to mechanical means to reduce the effective average particle size. The concentration of the surface modifier (weight by weight percentage) can vary from about 0.1% to about 90%, preferably from about 0.5% to about 80%, and more preferably is approximately 7% (w/v).

The premix can be used directly by subjecting it to mechanical means to reduce the effective average particle size in the dispersion to the desired particle size. It is preferred that the premix be used directly when a ball mill is used for attrition. Alternatively, the antipsychotic agent and, optionally, the surface modifier, can be dispersed in the liquid medium using suitable agitation such as, for example, a roller mill or a Cowles type mixer, until a homogeneous dispersion is achieved.

The mechanical means applied to reduce the effective average particle size of the antipsychotic conveniently can take the form of a dispersion mill. Suitable dispersion mills include a ball mill, an attritor mill, a vibratory mill, a planetary mill, media mills-such as a sand mill and a bead mill. A media mill is preferred due to the relatively shorter milling time required to provide the desired reduction in particle size. For media milling, in some embodiments, the apparent viscosity of the premix preferably is anywhere between about 0.1 Pa·s and about 1 Pa·s. In some embodiments, for ball milling, the apparent viscosity of the premix preferably is anywhere between about 1 mPa·s and about 100 mPa·s.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of the material for the grinding media is believed not to be critical. However, about 95% ZrO stabilized with magnesia, zirconium silicate, and glass grinding media provide particles which are acceptable for the preparation of pharmaceutical compositions. Further, other media, such as polymeric beads, stainless steel, titania, alumina and about 95% ZrO stabilized with yttrium, are useful. Preferred grinding media have a density greater than about 2.5 g/cm$^3$ and include about 95% ZrO stabilized with magnesia and polymeric beads.

The attrition time can vary widely and depends primarily upon the particular mechanical means and processing conditions selected. For rolling mills, processing times of up to two days or longer may be required for smaller size particles.

The particles are typically reduced in size at a temperature which does not significantly degrade the antipsychotic agent. Processing temperatures of less than about 30° C. to about 40° C. are ordinarily preferred. If desired, the processing equipment may be cooled with conventional cooling equipment. The method is conveniently carried out under conditions of ambient temperature and at processing pressures which are safe and effective for the milling process.

The surface modifier, if it was not present in the premix, is typically added to the dispersion after attrition in an amount, for example, as described for the premix above. Thereafter, the dispersion can be mixed by, for example, shaking vigorously. Optionally, the dispersion can be subjected to a sonication step using, for example, an ultrasonic power supply.

Aqueous compositions according to the present invention conveniently further comprise a suspending agent and a buffer, and optionally one or more of a preservative and an isotonizing agent. Particular ingredients may function as two or more of these agents simultaneously, e.g. behave like a preservative and a buffer, or behave like a buffer and an isotonizing agent.

Suitable suspending agents (also referred to as physical stabilizers) for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxy-propylene ethers. Preferably sodium carboxymethyl cellulose is used in a concentration of about 0.5 to about 2%, most preferably about 1% (w/v).

Suitable wetting agents preferred from the listed surfactant for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of about 0.5% to about 3%, more preferably about 0.5% to about 2%, most preferably about 1.1% (w/v).

Suitable buffering agents are salts of weak acids and should be used in amount sufficient to render the dispersion from about pH 6.0 to basic. Preferably, the pH is in a range of from about 6.0 to about 9.0; or in the range of from about 6.0 to about 8.0; or about 6.5 to about 7.5. For example, the pH is in the range of about 6.0 to about 6.5; or from about 6.5 to about 7.0; or from about 7.0 to about 7.5; or from about 7.5 to about 8.0; or from about 8.0 to about 8.5; or from about 8.5 to about 9.0. Particularly preferred is the use of a mixture of disodium hydrogen phosphate (anhydrous) (typically about 0.9%/o (w/v)) and sodium dihydrogen phosphate monohydrate (typically about 0.6% (w/v)). This buffer also renders the dispersion isotonic and, in addition, less prone to flocculation of the ester suspended therein.

Preservatives are antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-gamma-piccolinium chloride, phenylmercuric acetate and thimerosal. In particular, it is benzyl alcohol which can be used in a concentration up to about 2% (w/v), preferably up to about 1.5% (w/v).

Isotonizing agents are, for example, sodium chloride, dextrose, mannitol, sorbitol, lactose, sodium sulfate. The suspensions conveniently comprise from about 0% to about 10% (w/v) isotonizing agent. Mannitol may be used in a concentration from about 0% to about 7% more preferably, however, from about 1% to about 3% (w/v), especially from about 1.5% to about 2% (w/v) of one or more electrolytes are used to render the suspension isotonic, apparently because ions help to prevent flocculation of the suspended ester. In particular, electrolytes of the buffer serve as isotonizing agent.

A particularly desirable feature for an injectable formulation relates to the ease with which it can be administered. In particular such an injection should be feasible using a needle as fine as possible in a span of time which is as short as possible. This can be accomplished with the aqueous suspensions of the present invention by maintaining certain viscosities that can be easily taken up in a syringe (e.g. from a vial) and injected through a fine needle. For example, a PPIM viscosity is below about 75 mPa·s, or below about 60 mPa·s at room temperature, and a 23G, 1 inch needle, or a 22G, 1% inch needle is typically used For PP3M, a 22G, 1% inch needle, or a 22G, 1 inch needle is typically used. And for PP6M, a 20G, 1% inch needle is typically used.

Ideally, aqueous suspensions according to the present invention will comprise as much paliperidone palmitate as can be tolerated so as to keep the injected volume to a minimum, and as little of the other ingredients as possible.

In particular for PP3M or PP6M, the composition comprises, or consists essentially of, (a) from about 200 to about 500 mg/mL of paliperidone palmitate; (b) from about 2 to about 25 mg/mL of wetting agent; (c) from about 2.5 to about 50 mg/mL of one or more buffering agents; (d) from about 25 to about 150 mg/mL of a suspending agent; (e) optionally up to about 2% (w/v) preservatives; and (f) water q.s. ad 100%. Typically, the PP3M or PP6M composition has a pH of from about 6.0 to about 8.0, preferably about a pH of from 6.5 to about 7.5.

In other embodiments, for PP3M or PP6M, the composition comprises, or consists essentially of, (a) from about 250 to about 400 mg/mL of paliperidone palmitate; (b) from about 5 to about 20 mg/mL of wetting agent; (c) from about 5 to about 25 mg/mL of one or more buffering agents; (d)

from about 50 to about 100 mg/mL of a suspending agent; (e) optionally up to about 2% (w/v) preservatives; and (f) water q.s. ad 100%.

In other embodiments, for PP3M or PP6M, the composition comprises, or consists essentially of, (a) from about 280 to about 350 mg/mL of paliperidone palmitate; (b) from about 8 to about 12 mg/mL of wetting agent; (c) from about 5 to about 15 mg/mL of one or more buffering agents; (d) from about 65 to about 85 mg/mL of a suspending agent; (e) optionally up to about 2% (w/v) preservatives; and (f) water q.s. ad 100%/o.

In certain embodiments, the active ingredient in PP3M or PP6M is paliperidone palmitate (about 312 mg/mL). In certain embodiments, the inactive ingredients in PP3M or PP6M is polysorbate 20 (about 10 mg/mL), polyethylene glycol 4000 (about 75 mg/mL), citric acid monohydrate (about 7.5 mg/mL), sodium dihydrogen phosphate monohydrate (about 6 mg/mL), sodium hydroxide (about 5.4 mg/mL) and water for injection. An exemplified PP3M is disclosed in Example 2. An exemplified PP6M is disclosed in Example 3.

In particular, a composition for PP1M will comprise, or consist essentially of, by weight based on the total volume of the composition: (a) from about 1% to 50% (w/v) of the paliperidone palmitate; (b) from about 0.1% to 5% (w/v) of a wetting agent; (c) one or more buffering agents; (d) from about 0.1% to about 5% (w/v) of a suspending agent; (e) optionally up to about 2% (w/v) preservatives; and (f) water q.s. ad 100%. Typically, the PP1M composition has a pH of from about 6.0 to about 8.0, preferably a pH of from about 6.5 to about 7.5.

A composition PP1M will preferably comprise, or consistent essentially of, by weight based on the total volume of the composition: (a) from about 2% to 40% (w/v) of the paliperidone palmitate; (b) from about 0.25% to 3% (w/v) of a wetting agent; (c) one or more buffering agents; (d) from about 0.25% to about 3% (w/v) of a suspending agent; (e) optionally up to about 2% (w/v) preservatives; and (f) water q.s. ad 100%.

A composition for PP1M will more preferably comprise, or consist essentially of, by weight based on the total volume of the composition: (a) from about 3% to 20% (w/v) of the paliperidone palmitate; (b) from about 0.5% to 2% (w/v) of a wetting agent; (c) one or more buffering agents; (d) from about 0.5% to about 2% (w/v) of a suspending agent; (e) optionally up to about 2% (w/v) preservatives; and (t) water q.s. ad 100%.

In particular for PP1M, the composition comprises, or consists essentially of, (a) from about 50 to about 250 mg/mL of paliperidone palmitate; (b) from about 2 to about 25 mg/mL of wetting agent; (c) from about 2.5 to about 50 mg/mL of one or more buffering agents; (d) from about 5 to about 75 mg/mL of a suspending agent; (e) optionally up to about 2% (w/v) preservatives, and (f) water q.s. ad 100%.

In other embodiments, for PP1M, the composition comprises, or consists essentially of, (a) from about 100 to about 200 mg/mL of paliperidone palmitate; (b) from about 5 to about 20 mg/mL of wetting agent; (c) from about 5 to about 25 mg/mL of one or more buffering agents; (d) from about 10 to about 50 mg/mL of a suspending agent; (e) up to about 2% (w/v) preservatives, and (t) water q.s. ad 100%.

In other embodiments, for PP1M, the composition comprises, or consists essentially of, (a) from about 140 to about 180 mg/mL of paliperidone palmitate; (b) from about 8 to about 16 mg/mL of wetting agent; (c) from about 5 to about 15 mg/mL of one or more buffering agents; (d) from about 20 to about 40 mg/mL of a suspending agent; (e) optionally up to about 2% (w/v) preservatives; and (f) water q.s. ad 100%.

Most preferably, the active ingredient in PP1M is paliperidone palmitate (about 156 mg/mL). Most preferably, the inactive ingredients in PP1M is polysorbate 20 (about 12 mg/mL), polyethylene glycol 4000 (about 30 mg/mL), citric acid monohydrate (about 5 mg/mL), sodium dihydrogen phosphate monohydrate (about 2.5 mg/mL), disodium hydrogen phosphate anhydrous (about 5 mg/mL), sodium hydroxide (about 2.84 mg/mL) and water for injection. An exemplified PP1M is disclosed in Example 1.

Preferably an aqueous suspension will be made under sterile conditions and no preservatives will be used. Appropriate methods to aseptically prepare paliperidone palmitate are described in WO 2006/114384 which is hereby incorporated by reference herein.

The preferred aqueous dosage form contains inactive ingredients that are polysorbate 20, polyethylene glycol 4000, citric acid monohydrate, disodium hydrogen phosphate anhydrous, sodium dihydrogen phosphate monohydrate, sodium hydroxide, and water for injection.

A dose or dosing is typically expressed as milligrams (mg) of paliperidone palmitate.

Regarding six month interval dosing, paliperidone palmitate dosing may also be expressed as mg equivalents (mg eq.) of paliperidone with about 1092 and 1560 mg of paliperidone palmitate being equivalent to about 700 and 1000 mg eq. of paliperidone, respectively. For six-month dosing it is preferred to dose patients with about 700 mg eq. to about 1000 mg eq. paliperidone or about 1092 mg to about 1560 mg paliperidone palmitate.

Regarding three month interval dosing, paliperidone palmitate dosing may also be expressed as mg equivalents (mg eq.) of paliperidone with about 273, 410, 546, and 819 mg of paliperidone palmitate being equivalent to about 175, 263, 350, and 525 mg eq., of paliperidone, respectively. For three-month dosing it is preferred to dose patients with about 175 mg eq. to about 525 mg eq. paliperidone or about 273 mg to about 819 mg paliperidone palmitate.

Regarding one month interval dosing, paliperidone palmitate dosing may also be expressed as mg equivalents (mg eq.) of paliperidone with about 39, 78, 117, 156, and 234 mg of paliperidone palmitate being equivalent to about 25, 50, 75, 100 and 150 mg eq, of paliperidone, respectively. For one month dosing it is preferred to dose patients with about 25 mg eq. to about 150 mg eq. paliperidone or about 39 mg to about 234 mg paliperidone palmitate; or about 100 mg eq. to about 150 mg eq. paliperidone or about 156 mg to about 234 mg paliperidone palmitate, such as about 156 mg paliperidone palmitate or about 234 mg paliperidone palmitate.

The term "antipsychotics" or "antipsychotic drug medication" as used herein means any medication used to decrease or ameliorate the symptoms of psychosis in a person with a psychotic disorder.

The term "psychiatric patient" as used herein, refers to a human, who has been the object of treatment, or experiment for a "mental disorder" and "mental illness" refer to those provided in the Diagnostic and Statistical Manual Fifth Edition (DSM 5), American Psychiatric Association (APA). Those of ordinary skill in the art will appreciate that paliperidone esters (e.g. paliperidone palmitate) can be administered to psychiatric patients for all the known uses of risperidone. These mental disorders include, but are not limited to, schizophrenia; bipolar disorder or other disease states in which psychosis, aggressive behavior, anxiety or depression is evidenced. As set forth in DSM-5, schizophrenia refers to conditions characterized as schizophrenia, schizoaffective disorder and schizophreniform disorders. Bipolar Disorder refers to a condition characterized as a Bipolar Disorder, including Bipolar I and Bipolar Disorder II. The DSM was prepared by the Task Force on Nomenclature and Statistics of the American Psychiatric Association, and provides clear descriptions of diagnostic categories. Pathologic psychological conditions, which are psychoses or may be associated with psychotic features, include, but are not limited to the following disorders that have been characterized in the DSM. Diagnostic and Statistical Manual of Mental Disorders, Revised, 5th Ed. (2013). The skilled artisan will recognize that there are alternative nomenclatures, nosologies, and classification systems for pathologic psychological conditions and that these systems evolve with medical scientific progress. Examples of pathologic psychological conditions which may be treated include, but are not limited to, Mild Intellectual Disability, Moderate Intellectual Disability, Severe Intellectual Disability, Profound Intellectual Disability, Intellectual Disability Severity Unspecified, Autistic Disorders, Rett's Disorder, Childhood Disintegrative Disorders, Asperger's Disorder, Pervasive Developmental Disorder Not Otherwise Specified, Attention-Deficit/Hyperactivity Disorder Combined Type, Attention-Deficit/Hyperactivity Disorder Predominately Inattentive Type, Attention-Deficit/Hyperactivity Disorder Predominately Hyperactive-Impulsive Type, Attention-Deficit/Hyperactivity Disorder NOS, Conduct Disorder (Childhood-Onset and Adolescent Type, Oppositional Defiant Disorder, Disruptive Behavior Disorder Not Otherwise Specified, Solitary Aggressive Type, Conduct Disorder, Undifferentiated Type, Tourette's Disorder, Chronic Motor Or Vocal Tic Disorder, Transient Tic Disorder, Tic Disorder NOS, Alcohol Intoxication Delirium, Alcohol Withdrawal Delirium, Alcohol-Induced Persisting Dementia, Alcohol-Induced Psychotic Disorder with Delusions, Alcohol-Induced Psychotic Disorder with Hallucinations, Amphetamine or Similarly Acting Sympathomimetic Intoxication, Amphetamine or Similarly Acting Sympathomimetic Delirium, Amphetamine or Similarly Acting Sympathomimetic Induced Psychotic with Delusions, Amphetamine or Similarly Acting Sympathomimetic Induced Psychotic with Hallucinations, Cannabis-Induced Psychotic Disorder with Delusions, Cannabis-Induced Psychotic Disorder with Hallucinations, Cocaine Intoxication, Cocaine Intoxication Delirium, Cocaine-Induced Psychotic Disorder with Delusions, Cocaine-induced Psychotic Disorder with Hallucinations, Hallucinogen Intoxication, Hallucinogen Intoxication Delirium, Hallucinogen-Induced Psychotic disorder with Delusions, Hallucinogen-Induced Psychotic disorder with Delusions, Hallucinogen-Induced Mood Disorder, Hallucinogen-Induced Anxiety Disorder, Hallucinogen-Related Disorder Not Otherwise Specified, Inhalant Intoxication, Inhalant Intoxication Delirium, Inhalant-Induced Persisting Dementia, Inhalant-Induced Psychotic Disorder with Delusions, Inhalant-Induced Psychotic with Hallucinations, Inhalant-Induced Mood Disorder, Inhalant-Induced Anxiety Disorder, Inhalant-Related Disorder Not Otherwise Specified, Opioid Intoxication Delirium, Opioid-Induced Psychotic Disorder with Delusions, Opioid Intoxication Delirium, Opioid-Induced Psychotic Disorder with Hallucinations, Opioid-Induced Mood Disorder, Phencyclidine (PCP) or Similarly Acting Arylcyclohexylamine Intoxication, Phencyclidine (PCP) or Similarly Acting Arylcyclohexylamine Intoxication Delirium, Phencyclidine (PCP) or Similarly Acting Arylcyclohexylamine Induced Psychotic Disorder with Delusions, Phencyclidine (PCP) or Similarly Acting Arylcyclohexylamine Induced Psychotic Disorder with Hallucinations, Phencyclidine (PCP) or Similarly Acting Arylcyclohexylamine Mood Disorder, Phencyclidine (PCP) or Similarly Acting Arylcyclohexylamine Induced Anxiety Disorder, Phencyclidine (PCP) or Similarly Acting Arylcyclohexylamine Related Disorder Not Otherwise Specified, Sedative, Hypnotic or Anxiolytic Intoxication, Sedation, Hypnotic or Anxiolytic Intoxication Delirium, Sedation, Hypnotic or Anxiolytic Withdrawal Delirium, Sedation, Hypnotic or Anxiolytic Induced Persisting Dementia, Sedation, Hypnotic or Anxiolytic-Induced Psychotic Disorder with Delusions, Sedation, Hypnotic or Anxiolytic-Induced Psychotic Disorder with Hallucinations, Sedation, Hypnotic or Anxiolytic-Induced Mood Disorder, Sedation, Hypnotic or Anxiolytic-Induced Anxiety Disorder, Other (or Unknown) Substance Intoxication, Other (or Unknown) Substance-Induced Delirium, Other (or Unknown) Substance-Induced Persisting Dementia, Other (or Unknown) Substance-Induced Psychotic Disorder with Delusions, Other (or Unknown) Substance-Induced Psychotic Disorder with Hallucinations, Other (or Unknown) Substance-Induced Mood Disorder, Other (or Unknown) Substance-Induced Anxiety Disorder, Other (or Unknown) Substance Disorder Not Otherwise Specified, Obsessive Compulsive Disorder, Post-traumatic Stress Disorder, Generalized Anxiety Disorder, Anxiety Disorder Not Otherwise Specified. Body Dysmorphic Disorder, Hypochondriasis (or Hypochondriacal Neurosis), Somatization Disorder, Undifferentiated Somatoform Disorder, Somatoform Disorder Not Otherwise Specified, Intermittent Explosive Disorder, Kleptomania, Pathological Gambling, Pyromania, Trichotillomania, and Impulse Control Disorder NOS, Schizophreniform Disorder, Schizoaffective Disorder, Delusional Disorder, Brief Psychotic Disorder, Shared Psychotic Disorder, Psychotic Disorder Due to a General Medical Condition with Delusions, Psychotic Disorder Due to a General Medical Condition with Hallucinations, Psychotic Disorders Not Otherwise Specified, Major Depression, Single Episode, Severe, without Psychotic Features, Major Depression, Recurrent, Severe, without Psychotic Features, Bipolar Disorder, Mixed, Severe, without Psychotic Features, Bipolar Disorder, Mixed, Severe, with Psychotic Features, Bipolar Disorder, Manic, Severe, without Psychotic Features, Bipolar Disorder, Manic, Severe, with Psychotic Features, Bipolar Disorder, Depressed, Severe, without Psychotic Features, Bipolar Disorder, Depressed, Severe, with Psychotic Features, Bipolar II Disorder, Bipolar Disorder Not Otherwise Specified, Personality Disorders, Paranoid, Personality Disorders, Schizoid, Personality Disorders, Schizotypal, Personality Disorders, Antisocial, and Personality Disorders, Borderline.

The term "therapeutically effective amount" as used herein, means that amount of active compound or pharmaceutical agent that elicits the biological or medicinal response in human that is being sought by a researcher, medical doctor or other clinician, which includes alleviation of the symptoms of the disease or disorder being treated.

Those of skill in the treatment of diseases could determine the effective amount of paliperidone to administer for the treatment of the diseases listed above. By way of example, an effective amount of paliperidone for the treatment of mental disorders would be from about 0.01 mg/kg to about 2 mg/kg body weight per day. For semi-annual dosing it is preferred to dose patients with about 700 mg-eq. to about 1000 mg eq. paliperidone or about 1092 mg to about 1560 mg paliperidone palmitate. The amount of paliperidone palmitate is provided in sufficient amount to provide the equivalent dose of paliperidone after the palmitic acid moiety is removed from the ester (e.g. 1560 mg corresponds to paliperidone 1000 mg). For six-month dosing it is preferred to dose patients with about 700 mg eq to about 1000 mg eq. paliperidone or about 1092 mg to about 1560 mg paliperidone palmitate.

The following Examples are provided to illustrate some of the concepts described within this disclosure. While the Examples are considered to describe certain embodiments, they should not be considered to limit the more general embodiments described herein. The following non-limiting examples are provided to further support the present disclosure. Unless otherwise noted, references to PP1M, PP3M and PP6M in Examples 4-9 refer to the formulations described in Example 1 (PPIM), Example 2 (PP3M) and Example 3 (PP6M).

Example 1: One-Month Extended Release Formulation (PP1M)

Table 2 below includes an exemplary one-month extended release formulation (PP1M) of 100 mg/mL eq. paliperidone suitable for intramuscular (IM) injection.

TABLE 2

| PP1M | |
|---|---|
| Component | Concentration (mg/mL) |
| Paliperidone Palmitate | 156 |
| Polysorbate 20 | 12 |
| Polyethylene Glycol 4000[1] | 30 |
| Citric Acid Monohydrate | 5 |
| Disodium Hydrogen Phosphate, Anhydrous | 5 |
| Sodium Dihydrogen Phosphate Monohydrate | 2.5 |
| Sodium Hydroxide | 2.84 |
| Water for Injection | q.s. ad 1000 µL |

The PPIM can be provided in a prefilled syringe, with dosage strengths ranging from 25 mg eq. to 150 mg eq. obtained by filling the syringes with different volumes of a 100 mg/mL eq. bulk suspension. Table 3 shows the different dosage strengths, including syringe size and nominal fill volume

TABLE 3

| PP1M Dosage Strengths with Syringe Size and Fill Volume | | |
|---|---|---|
| Strength (mg) | Syringe Size | Nominal Fill Volume (mL) |
| eq. 25 | 0.5 mL | 0.250 |
| eq. 50 | 0.5 mL | 0.500 |
| eq. 75 | 1 mL Long | 0.750 |
| eq. 100 | 1 mL Long | 1.000 |
| eq. 125 | 2.25 mL | 1.250 |
| eq. 150 | 2.25 mL | 1.500 |

Table 4 describes the syringe components used to package the PP1M.

TABLE 4

| Syringe Components for PP1M | |
|---|---|
| Component | Description |
| Syringe Barrel | Transparent Cyclic Olefin Copolymer (COC) with Integrated Luer Lock Sizes of 0.5 mL, 1 mL Long or 2.25 mL |
| Tip Cap | Bromobutyl Rubber, Dark Grey |
| Plunger Stopper | FluroTec © Coated Bromobutyl Rubber, Dark Grey (1 mL Long used for 0.5 mL syringe and 1 mL Long syringe; 1-3 mL used for 2.25 mL syringe) |

Example 2: Three Month Extended Release Formulation (PP3M)

Table 5 below includes an exemplary three-month extended release formulation (PP3M) of 200 mg/mL eq paliperidone suitable for intramuscular (IM) injection

TABLE 5

| PP3M | |
|---|---|
| Component | Concentration (mg/mL) |
| Paiiperidone Palmitate | 312 |
| Polysorbate 20 | 10 |
| Polyethylene Glycol 4000 | 75 |
| Citric Acid Monohydrate | 7.5 |
| Sodium Dihydrogen Phosphate Monohydrate | 6 |
| Sodium Hydroxide | 5.4 |
| Water for Injection | q.s. ad 1 mL |

The PP3M can be provided in a prefilled syringe, with dosage strengths ranging from 175 mg eq to 525 mg eq. obtained by filling the syringes with different volumes of a 200 mg/mL eq. bulk suspension. Table 6 shows the different dosage strengths, including syringe size and nominal fill volume.

TABLE 6

| PP3M Dosage Strengths with Syringe Size and Fill Volume | | | |
|---|---|---|---|
| Dose as Paliperidone Palmitate (mg) | Dose Equivalent as Paliperidone (mg) | Syringe Size | Nominal Fill Volume (mL) |
| 273 | 175 | 1 mL Long | 0.875 |
| 410 | 263 | 2.25 mL | 1.315 |
| 546 | 350 | 2.25 mL | 1.750 |
| 819 | 525 | 2.8 mL | 2.625 |

Table 7 describes the syringe components used to package the PP3M.

TABLE 7

| Syringe Components for PP3M | |
|---|---|
| Component | Description |
| Syringe Barrel | Transparent Cyclic Olefin Copolymer (COC) with Integrated Luer Lock Sizes of 1 mL Long, 2.25 mL or 2.8 mL |
| Tip Cap | Bromobutyl Rubber, Dark Grey |
| Plunger | FluroTec © Coated Bromobutyl Rubber, Dark Grey |

TABLE 7-continued

Syringe Components for PP3M

| Component | Description |
|---|---|
| Stopper | (1 mL Long used for 1 mL Long syringe; and 1-3 mL used for 2.25 mL syringe and 2.8 mL syringe) |

Example 3: Six Month Extended Release Formulation (PP6M)

Table 8 below includes an exemplary six-month extended release formulation (PP6M) of 200 mg/mL eq. paliperidone palmitate suitable for intramuscular (IM) injection

TABLE 8

PP6M

| Component | Concentration (mg/mL) | Unit Dose (mg/syringe in 3.5 mL Dose) | Unit Dose (mg/syringe in 5.0 mL Dose) |
|---|---|---|---|
| Paliperidone Palmitate | 312 | 1092 | 1560 |
| Polysorbate 20 | 10 | 35 | 50 |
| Polyethylene Glycol 4000 | 75 | 262.5 | 375 |
| Citric Acid Monohydrate | 7.5 | 26.25 | 37.5 |
| Sodium Dihydrogen Phosphate Monohydrate | 6 | 21 | 30 |
| Sodium Hydroxide | 5.4 | 18.9 | 27 |
| Water for Injection | q.s. ad 1.0 mL | q.s. ad 3.5 mL | q.s. ad 5.0 mL |

The PP6M can be provided in a prefilled syringe, with dosage strengths ranging from 700 mg eq. to 1000 mg eq. obtained by filling the syringes with different volumes of a 200 mg/mL eq. bulk suspension. Table 9 shows the different dosage strengths, including syringe size and nominal fill volume

TABLE 9

PP6M Dosage Strengths with Syringe Size and Fill Volume

| Dose as Paliperidone Palmitate (mg) | Dose Equivalent as Paliperidone (mg) | Syringe Size | Nominal Fill Volume (mL) |
|---|---|---|---|
| 1092 | 700 | 5 mL | 3.5 |
| 1560 | 1000 | 5 mL | 5.0 |

Table 10 describes the syringe components used to package the six-month extended release formulation

TABLE 10

Syringe Components PP6M

| Component | Description |
|---|---|
| Syringe Barrel | Transparent Cyclic Olefin Copolymer (COC) with Integrated Luer Lock |
| Tip Cap | Bromobutyl Rubber |
| Plunger Stopper | Bromobutyl Rubber |
| Plunger Rod | Polypropylene |
| Backstop (aka Finger Flange) | Homopolypropylene |

Example 4: A Double-Blind, Randomized, Active-Controlled, Parallel-Group Study of Paliperidone Palmitate 6-Month Formulation Study Design A randomized, double-blind, active-controlled, multi-center, interventional, parallel-group non-inferiority study. A flow chart of the study design is shown in FIG. 1. All eligible subjects who progressed without relapse participated in a Screening Phase (of up to 28 days), a Maintenance Phase that included 1 injection cycle with either PPIM or PP3M (yielding a phase duration of 1 or 3 months, accordingly), and a Double-blind Phase (of 12 months). The Double-blind Phase was designed to include 4 injection cycles of PP3M (active control), or 2 injection cycles of PP6M (investigational drug with alternating placebo).

Before the Maintenance Phase, some subjects participated in a Transition Phase, with 1 to 5 injections of PP1M, if they entered the study on an oral antipsychotic, on injectable risperidone, or on PP1M previously initiated but not yet stabilized. The combined Transition and Maintenance phases is referred to hereafter as the Open-Label Phase.

Randomization: 702 subjects were randomized in a 1:2 ratio to PP3M (n=224) or PP6M (n=478) treatment groups. The randomization was stratified by study center and by the maintenance dose level (moderate or high).

Primary analysis population for efficacy: Double-blind Intent-to-Treat (DB ITT) analysis set, defined as all randomized subjects who received at least 1 dose of double-blind study medication.

Primary efficacy variable: the percentage of subjects who have not relapsed at the end of the 12-month Double-blind Phase based on the Kaplan-Meier cumulative estimate of survival.

Additional Analysis Population for efficacy: Per-protocol analysis set, defined as all randomized subjects who received at least 1 dose of double-blind study medication and did not have major protocol violations, that is, major protocol deviations that may impact efficacy such as violations of intended study population, errors in treatment assignment or use of excluded medication.

Analysis population for safety: same as DB ITT.

Planned sample size: The sample size for the Double-blind Phase of the study was 549 randomized subjects, based on determinations to provide a minimum of 80% power for the primary endpoint. The sample size determination includes the assumptions that the expected survival rate (percentage of subjects remaining relapse-free at 12 months) in the PP3M group is 85%, and that the 1-sided significance level should be 2.5% Given these assumptions, 549 subjects randomized in a 1:2 ratio (PP3M:PP6M) were required to demonstrate with 80% power that PP6M was no worse than PP3M by a noninferiority margin of 10% for the percentage of subjects remaining relapse-free at 12 months.

Primary Objective

The primary efficacy objective is to demonstrate that injection cycles consisting of a single administration of PP6M (700 or 1000 mg eq.) are not less effective than 2 sequentially administered injections of PP3M (350 or 525 mg eq.) for the prevention of relapse in subjects with schizophrenia previously stabilized on corresponding doses of PP1M (100 or 150 mg eq.) or PP3M (350 or 525 mg eq.).

Subject and Treatment Information

The study enrolled 841 subjects across 20 countries and 126 sites. Of those, 702 subjects were randomized to 1 of 2 treatment groups in a 1:2 ratio (224 in PP3M and 478 in PP6M). Among the 702 subjects in the DB ITT population, 23 subjects were excluded from the per-protocol population, the number of subjects included in the per-protocol analysis set is 217 and 462, for the PP3M and PP6M treatment groups, respectively. In the DB ITT analysis set, 521 (74.2%) of the subjects were white and 480 (68.4%) were male. The mean (SD) age was 40.8 (11.53) years, ranging from 18 to 69 years.

Of the 702 randomized subjects, 571 (81.3%) subjects completed the 12-month Double-blind Phase without a relapse event, and 47 (6.7%) subjects completed the Double-blind Phase by having a relapse event. The most frequent reason for withdrawal was 'Withdrawal by subject' by 54 (7.7%) subjects.

Efficacy

The primary efficacy endpoint was the percentage of subjects who have not relapsed by the end of the 12-month Double-blind Phase based on the Kaplan-Meier 12-Month cumulative estimate of survival. Statistical analysis tests were conducted at the two-sided 0.05 significance level.

Primary Efficacy Endpoint

Figure 2:
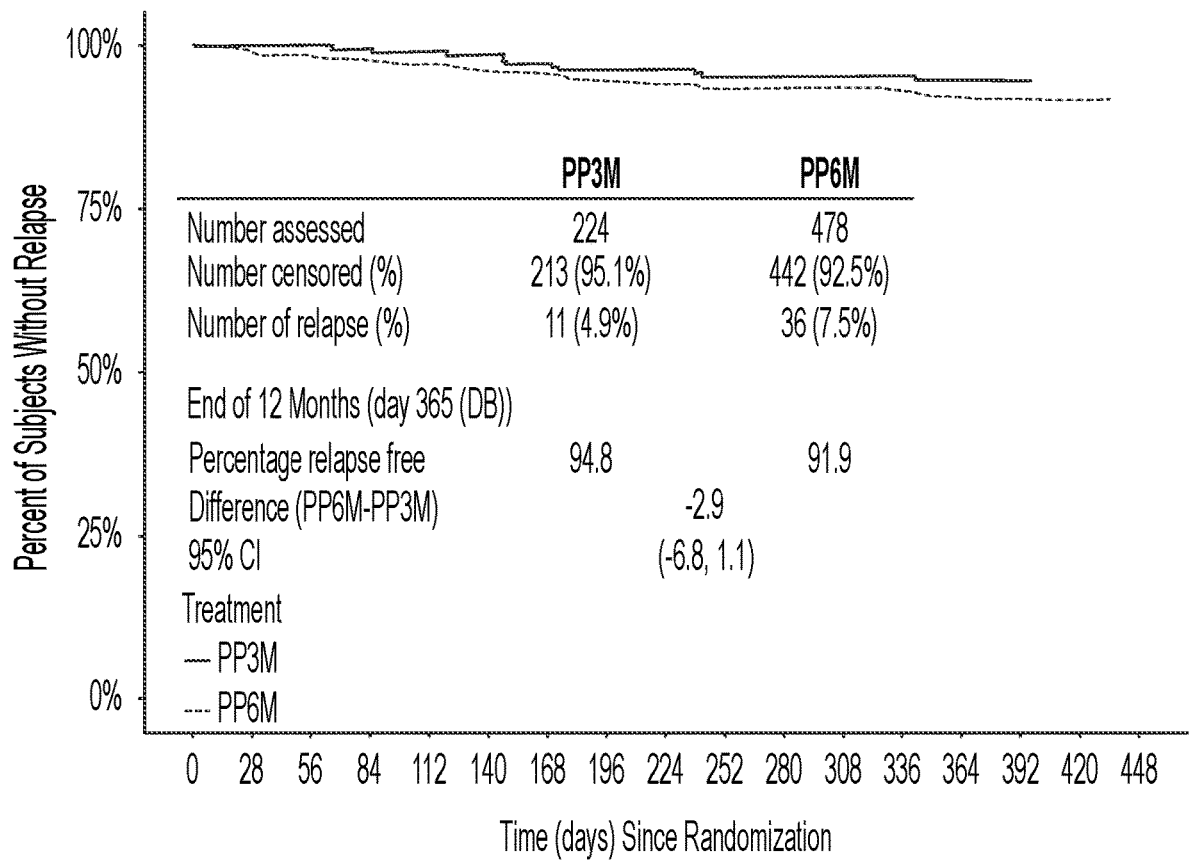
FIG. 2 depicts a Kaplan-Meier plot of time to relapse during the double-blind phase up to month 12.

In the DB ITT population, 11 (4.9%) subjects in the PP3M group and 36 (7.5%) subjects in the PP6M group experienced a relapse event during the 12 Month Double-blind Phase. The estimated difference (95% CI) between the treatment groups (PP6M-PP3M) in percentages of subjects who remained relapse free is −2.9% (−6.8%, 1.1%). The lower bound of the 95% confidence interval is larger than the pre-specified non-inferiority margin of −10%, therefore, PP6M can be declared to be non-inferior to PP3M (FIG. 2).

Figure 3:
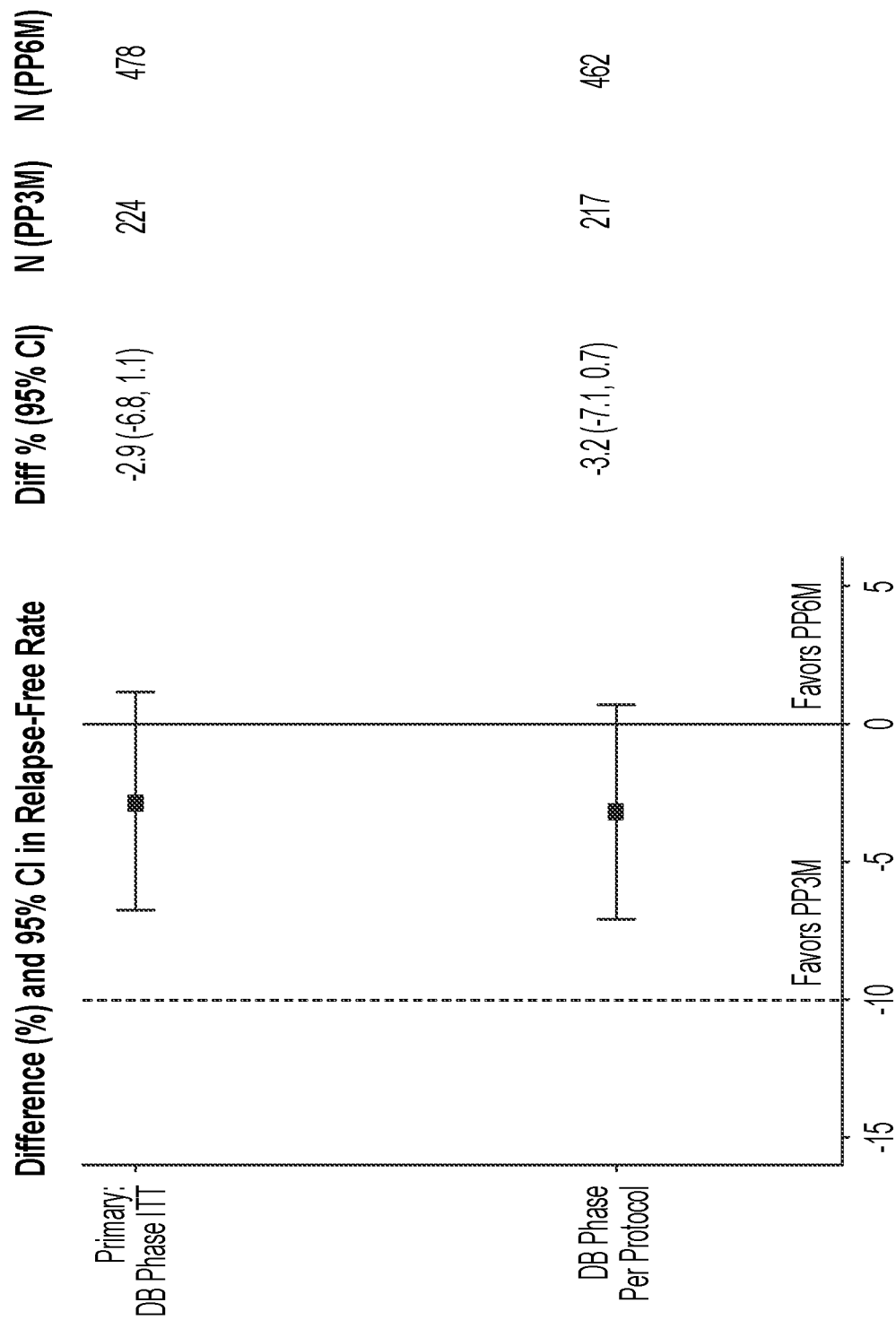
FIG. 3 depicts a Forest plot of estimated percentage (95% CI) of subjects that remained relapse free at month 12.

In the per-protocol analysis population, 10 (4.6%) subjects in the PP3M group and 35 (7.6%) subjects in the PP6M group experienced a relapse event during the Double-blind Phase. The results are similar to that obtained for the DB ITT analysis population, further confirming the non-inferiority of PP6M to PP3M (FIG. 3).

Supplementary analyses were conducted for the primary efficacy analysis by including data collected during the follow-up phase for subjects who withdrew from the Double-blind phase. Results are consistent with primary efficacy analysis.

For the DB ITT analysis population, the ratio (95% CI) of the instantaneous risk (hazard) of relapse for a subject in the PP6M treatment group during the Double-blind Phase versus the risk for a subject in the PP3M in the Double-blind Phase was 1.57 (95% CI: 0.8, 3.08), based upon a Cox Proportional Hazards Model with treatment as the only factor. Accordingly, the hazard rate in the PP6M subjects is 1.57 times the hazard rate of PP3M treated subjects.

Safety

Overall, 297/478 (62.1%) subjects in the PP6M group and 131/224 (58.5%) subjects in the PP3M group experienced at least one TEAE during the Double-blind Phase. The most common (≥5%) TEAEs during the Double-blind Phase were weight increased (8.4%), injection site pain (7.7%), headache (6.7%), upper respiratory tract infection (5.0%) for the PP6M group, and weight increased (7.6%), nasopharyngitis (5.8%), headache (5.4%) for the PP3M group.

There were 1 and 3 deaths in the Open-Label (combined Transition and Maintenance phases) and Double-blind Phases, respectively. Among the 3 deaths in the Double-blind Phase, 1 (0.2%) was for the PP6M group, and 2 (0.9%) were for the PP3M group.

Thirty-nine subjects (24 [5.0%] in PP6M, 15 [6.7%] in PP3M) experienced serious TEAEs during the Double-blind Phase.

During the Double-blind Phase, study medication was permanently stopped due to an adverse event with the following incidence across treatment groups:16 (3.3%) subjects in the PP6M group, and 6 (2.7%) subjects in the PP3M group.

ABBREVIATIONS

DB: double-blind.
OL: open-label.
MA: maintenance.
PANSS: positive and negative syndrome scale for schizophrenia.
PP: per-protocol.
KM: Kaplan-Meier.
ITT intent to treat.
SD: standard deviation.
CI confidence interval.
TEAE: treatment-emergent adverse event.

Example 5: Dosing Conversion

Conversion from PP1M or PP3M to PP6M doses are described in Table 11 below.

TABLE 11

| Paliperidone palmitate Dosing Conversion Tables | |
| --- | --- |
| PP6M Doses for Adult Patients Adequately Treated with PP1M | |
| If the Last Dose of PP1M is: | Transition to PP6M dose of: |
| 156 mg (100 mg eq.) | 1092 mg (700 mg eq.) |
| 234 mg (150 mg eq.) | 1560 mg (1000 mg eq.) |
| PP6M Doses for Adult Patients Adequately Treated with PP3M | |
| If the Last Dose of PP3M is: | Transition to PP6Mdose of: |
| 546 mg (350 mg eq.) | 1092 mg (700 mg eq.) |
| 819 mg (525 mg eq.) | 1560 mg (1000 mg eq.) |

Patients who are adequately treated with either PP1M (after at least 4 months of treatment) or PP3M (at least one 3-month injection cycle) and do not require dose adjustment may be switched to PP6M. PP6M should be initiated in place of the next scheduled dose of PP1M (±7 days) or PP3M (±14 days). The dose of PP6M should be based on the previous corresponding dose of PP3M or PP1M, as shown in Table 11, supra. When transitioning to PP6M from PP1M, to establish a consistent maintenance dose, it is recommended that the last two doses of PP1M be the same dosage strength before starting PP6M.

A prior treatment period with PP1M or PP3M ensures that paliperidone plasma concentrations are at or approach steady state prior to the transition to PP6M.

Model-based simulations suggest that subjects transitioning directly from PP1M (after at least 4-months of treatment) to PP6M have similar paliperidone exposure levels when compared to those subjects who transition from PP3M (after at least one 3-month injection cycle) to PP6M. Consequently, subjects may be transitioned directly from PP1M to PP6M, without transitioning to PP3M first prior to starting PP6M dosing.

Example 6—Pharmacokinetic Profile of PP6M in Subjects Transitioning from PP1M or PP3M Objective The objective of this trial was to assess the pharmacokinetic (PK) profile of PP6M (700 or 1000 mg eq.) administered in the gluteal muscle in subjects with schizophrenia who have transitioned from corresponding doses of PP1M (100 or 150 mg eq.) or PP3M (350 or 525 mg eq.).

Subjects and Methods

This clinical trial was a randomized, double-blind, active-controlled, multicenter, interventional, parallel-group study. All eligible subjects who progressed without relapse participated in a Screening Phase (of up to 28 days), a Maintenance Phase that included 1 injection cycle with either paliperidone palmitate 1-month (PP1M) or paliperidone palmitate 3-month (PP3M) (yielding a phase duration of 1 or 3 months, accordingly), and a double-blind Phase (of 12 months). The double-blind Phase was designed to include 2 injection cycles of paliperidone palmitate 6 month (PP6M) (investigational drug with alternating placebo) or 4 injection cycles of PP3M (active control). Multiple pharmacokinetic blood samples were collected during the open label phase (PP1M and PP3M) as well as double-blind phase (PP3M and PP6M) of the trial to determine the time course of paliperidone plasma concentrations. The aim of the PK evaluations was to characterize the time course of plasma paliperidone concentrations and PK parameters such as maximum and minimum plasma concentrations and their associated timing. Therefore, 3 PK samples were scheduled weekly around the expected paliperidone peak at approximately 1 month after the PP6M dose, and 6 PK samples were scheduled weekly when approaching the end of the 6-month dosing interval.

Results

Pharmacokinetics of Paliperidone in the Maintenance Phase after PP1M and PP3M Dosing After administration of PP1M in the Maintenance Phase, median $t_{max}$ after a 100 mg eq. dose was 8 days and was comparable to median $t_{max}$ of 7 days after a 150 mg eq. dose. After administration of 350 or 525 mg eq. (PP3M) median ta, was comparable and was 28 days. Based on visual inspection, $C_{trough}$, $C_{max}$, and $AUC_{3M}$ seemed to increase dose proportionally for both PP1M and PP3M. Dose-normalized mean $C_{trough}$, $C_{max}$, and $AUC_{3M}$ were comparable for PP1M and PP3M. The Peak/Trough Ratio was also comparable for PP1M and PP3M.

Pharmacokinetics of Paliperidone in the Double-Blind Phase after PP6M and PP3M Dosing.

Figure 4:
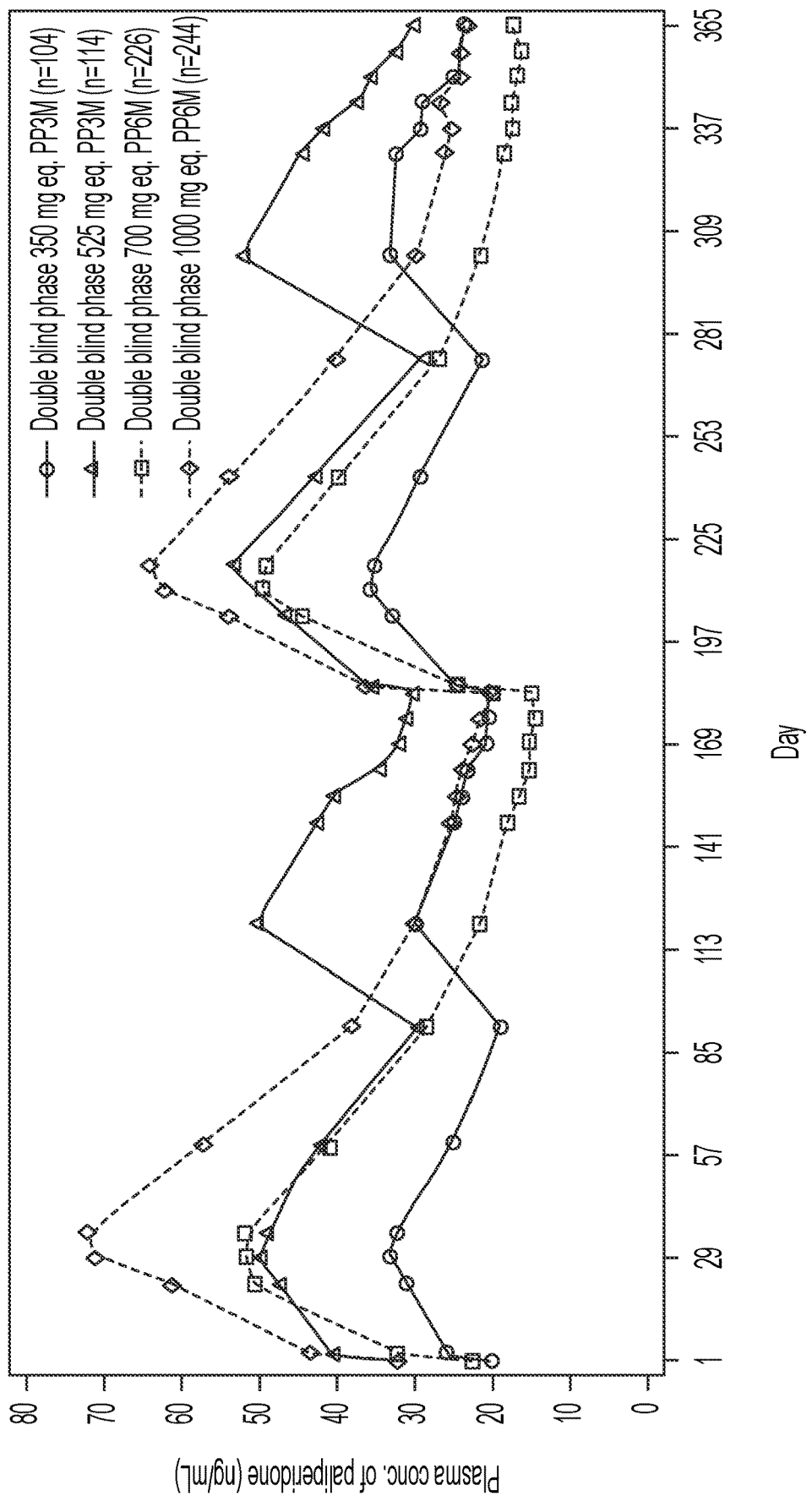
FIG. 4 depicts median plasma concentration time profiles of paliperidone after administration of PP3M (350 mg eq. or 525 mg eq.) and PP6M (700 mg eq. or 1000 mg eq.) in a double-blind study.

Mean dose-normalized trough concentrations were comparable for PP3M and PP6M at Day 1 (24.6 ng/mL and 25.0 ng/mL, respectively); at later timepoints the subjects who received PP6M had approximately 25-28% lower trough concentrations (16.7 ng/mL at Day 183 and 17.3 ng/mL at Day 365) compared to subjects who received PP3M (22.2 ng/mL at Day 183 and 24.1 ng/mL at Day 365). After the first administration of 350 or 525 mg eq. PP3M or 700 or 1000 mg eq. PP6M in the Double-blind Phase, median $t_{max}$ was comparable for all treatments, i.e., approximately 28 days. Similarly, after administration of 350 or 525 mg eq. PP3M or 700 or 1000 mg eq. PP6M in the second 6 months of the Double-blind Phase, median $t_{max}$ was comparable and ranged between 29 and 32 days. Based on visual inspection, $C_{trough}$, $C_{max}$, and $AUC_{6M}$ seemed to increase dose proportionally for PP6M (700 or 1000 mg eq.) after administration of each, the first and second dose, in the double-blind phase. Similarly, PK exposure parameters for paliperidone ($C_{trough}$, $C_{max}$, and $AUC_{6M}$) seem to be dose proportional, after the first and third doses of PP3M (350 or 525 mg eq.) in the Double-blind Phase. Dose-normalized mean $C_{max}$ was slightly higher (1.4 to 1.5-fold) for PP6M, when compared to PP3M. Mean dose normalized total paliperidone exposure ($AUC_{6M}$) was comparable in the Double-blind Phase after PP3M and PP6M dosing. The results are summarized below in Table 12, as well as in FIG. 4.

Median peak-to-trough ratios after PP3M administration in the Maintenance and Double-blind Phase were comparable across doses, ranging from 1.85 to 1.92 and 1.66 to 2.11 in the Maintenance- and Double-blind Phases, respectively. Median peak-to-trough ratios in the double blind phase after PP6M administrated once every six months ranged from 2.71-3.41. Median peak to trough ratios after PP6M administration in the Double-blind Phase were comparable across doses and were slightly higher after the first administration (ranging from 3.32 to 3.41) compared to the second administration (ranging from 2.71 to 3.20).

After stratification per administered dosage, maintenance phase product, injection site in maintenance phase, gender, age, and creatinine clearance category for several groups, no clinically meaningful difference was observed as the ranges were overlapping due to the high inter-subject variation for the PP3M and PP6M subgroups for $C_{max}$, $AUC_{6M}$.

Dose normalized mean paliperidone exposure ($C_{max}$, $AUC_{6M}$) after PP6M administration in the Double-blind Phase was comparable between sub-groups of subjects who receive PP1M or PP3M in the maintenance phase.

TABLE 12

PK Data for Patients Given PP3M and PP6M

| Paliperidone PK (mean [SD], $t_{max}$:median [range]) | PP3M (350 mg eq.) | PP3M (525 mg eq.) | PP6M (700 mg eq.) | PP6M (1000 mg eq.) |
|---|---|---|---|---|
| DB 0-6 Months | | | | |
| n | 98[a] | 112[b] | 222[c] | 229[d] |
| $t_{max}$ (h) | 670.80 (0.00-2256.57) | 679.92 (0.00-2325.15) | 671.09 (0.00-4367.42) | 674.00 (0.00-4366.57) |
| $t_{max}$ (days) | 27.95 (0.00-94.02) | 28.33 (0.00-96.88) | 27.96 (0.00-181.98) | 28.08 (0.00-181.94) |

TABLE 12-continued

PK Data for Patients Given PP3M and PP6M

| Paliperidone PK (mean [SD], $t_{max}$:median [range]) | PP3M (350 mg eq.) | PP3M (525 mg eq.) | PP6M (700 mg eq.) | PP6M (1000 mg eq.) |
|---|---|---|---|---|
| $C_{trough}$ (ng/mL) | 19.8 (9.82) | 34.1 (19.7) | 17.2 (11.5) | 23.2 (16.2) |
| $C_{max}$ (ng/mL) | 42.5 (23.7) | 67.0 (39.1) | 68.8 (40.4) | 93.6 (61.2) |
| $AUC_{3M}$ (ng · h/mL) | 64357 (31797) | 103499 (51173) | — | — |
| $AUC_{6M}$ (ng · h/mL) | 128713 (63593) | 206998 (102347) | 152555 (73249) | 204527 (97213) |
| DB 6-12 Months | | | | |
| n | 87[e] | 101[f] | 193[g] | 197[h] |
| $t_{max}$ (h) | 766.17 (23.67-2301.80) | 692.33 (44.62-2233.83) | 717.87 (43.33-4367.33) | 720.45 (0.00-3623.42) |
| $t_{max}$ (days) | 31.92 (0.99-95.91) | 28.85 (1.86-93.08) | 29.91 (1.81-181.97) | 30.02 (0.00-150.98) |
| $C_{trough}$ (ng/mL) | 22.7 (10.8) | 34.8 (20.6) | 17.6 (11.7) | 24.3 (12.8) |
| $C_{max}$ (ng/mL) | 44.1 (21.1) | 67.2 (55.1) | 67.9 (69.8) | 84.2 (47.0) |
| $AUC_{3M}$ (ng · h/mL) | 68410 (27774) | 103004 (57770) | — | — |
| $AUC_{6M}$ (ng · h/mL) | 136819 (55549) | 206009 (115541) | 143258 (66364) | 191933 (81831) |

[a] n = 92 for $C_{trough}$ and n = 97 for $AUC_{3M}$ and $AUC_{6M}$
[b] n = 108 for $C_{trough}$
[c] n = 182 for $C_{trough}$ and n = 215 for $AUC_{6M}$
[d] n = 181 for $C_{trough}$ and n = 222 for $AUC_{6M}$
[e] n = 82 for $C_{trough}$ and n = 84 for $AUC_{3M}$ and $AUC_{6M}$
[f] n = 95 for $C_{trough}$
[g] n = 160 for $C_{trough}$ and n = 185 for $AUC_{6M}$
[h] n = 177 for $C_{trough}$ and n = 194 for $AUC_{6M}$

Example 7—Dosing Window for PP6M Maintenance Treatment

Population PK Simulations: Effects of Extending or Shortening the Dosing Interval on the $C_{max}$ and $C_{trough}$ Acceptability of a dosing window 2 weeks before and 3 weeks after the regularly scheduled 6-month maintenance injection was evaluated as follows:

The moderate PP6M dose strength (700 mg eq.) was used to simulate the worst-case scenario where extending the dosing interval results in the lower $C_{trough}$. As shown in Table 13, for injections delayed by 1, 2 and 3 weeks relative to the scheduled 6-month injection after reaching PP6M steady state on 700 mg eq., the median $C_{trough}$ decreased from 15.8 ng/mL to 15.3 (−3.2%), 14.9 (−5.6%), and 14.4 (−8.9%) ng/mL, respectively; and The highest PP6M dose strength (1000 mg eq.) was used to simulate the worst-case scenario where shortening the dosing interval results in the highest $C_{max}$. As shown in Table 13, reproduced below, for injections administered 1 week earlier and 2 weeks earlier relative to the scheduled 6-month injection after reaching PP6M steady state on 1000 mg eq., the median $C_{max}$ increased from 76.1 ng/mL to 76.3 (+0.3%) and to 76.6 (+0.7%), respectively.

TABLE 13

Pharmaeokinetie Data at PP6M Steady State (dosing 1-2 weeks early and 1-3 weeks late relative to the scheduled 6-month injection)

| Dose | Regime | $C_{max}$ (ng/mL)[a] | % change vs base | $C_{trough}$ (ng/mL)[b] | % change vs base |
|---|---|---|---|---|---|
| High Dose | base PP6M | 76.1 | — | | |
| | 1 week earlier | 76.3 | +0.3% | | |
| | 2 weeks earlier | 76.6 | +0.7% | | |
| Moderate Dose | base PP6M | | | 15.8 | — |
| | 1 week later | | | 15.3 | −3.2% |
| | 2 weeks later | | | 14.9 | −5.7% |
| | 3 weeks later | | | 14.4 | −8.9% |

Figure 5:
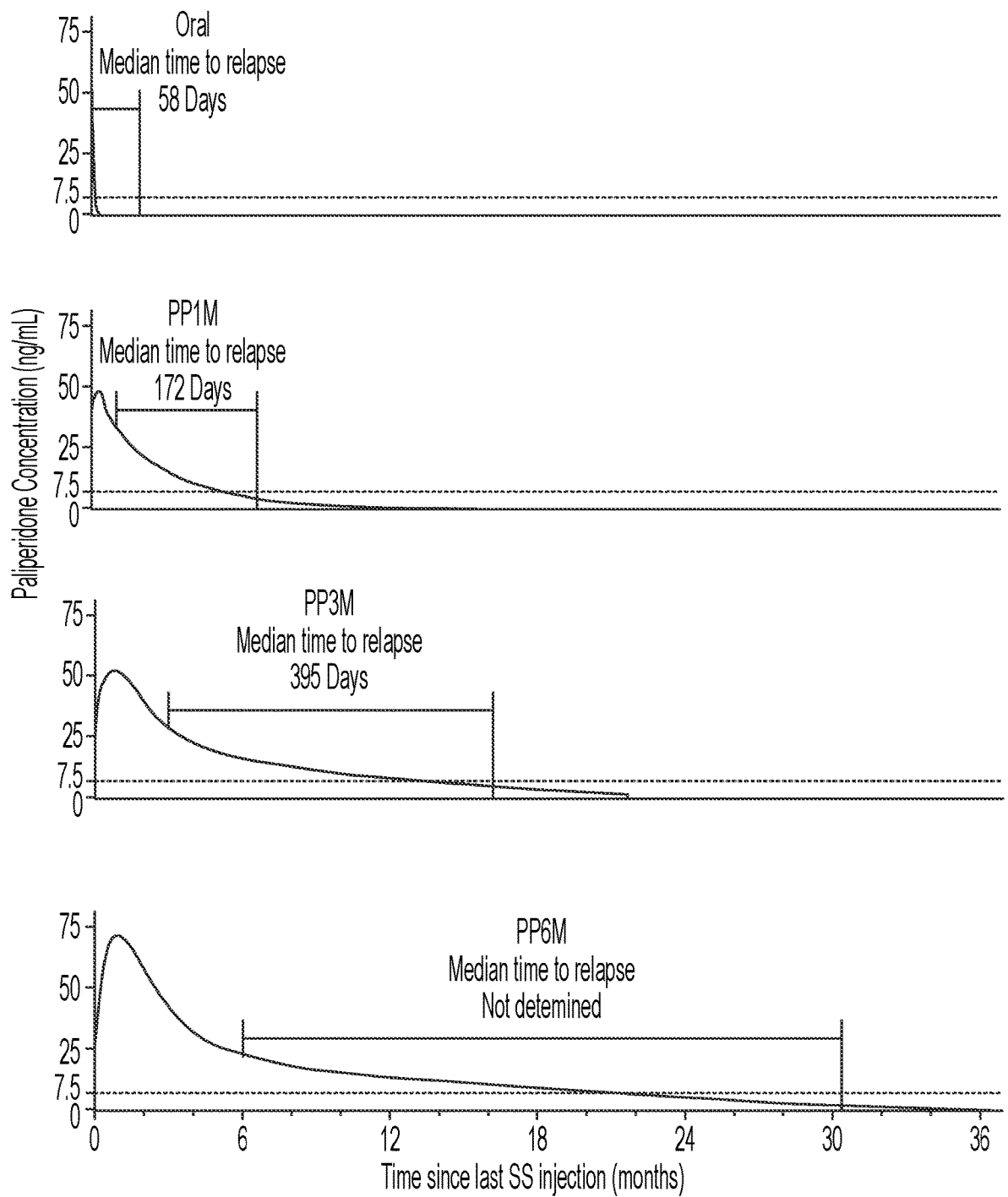
FIG. 5 depicts a comparison of PK plasma concentration and clinical efficacy (median time to relapse) across paliperidone formulations.

Duration of Clinical Effect Based on Median Time to Relapse in Relapse Prevention Studies PK simulations were conducted to evaluate the relationship between median time to relapse and the time point at which the median paliperidone concentration decreased to 7.5 ng/mL, following administration of the last steady-state dose in each study prior to the Double-blind phase (oral paliperidone ER 12 mg, PP1M 150 mg eq, PP3M 525 mg eq, and PP6M 1000 mg eq.), as shown in FIG. 5. An apparent delay lasting from several weeks to several months was observed between the time point when the median plasma paliperidone concentration decreased to 7.5 ng/mL and the median time to relapse, i.e., the time point when half of the subjects had experienced relapse, while the other half of the subjects either relapsed later or did not relapse during the study. Thus, it appears that the therapeutic effect is more prolonged than the expected effect based on the 7.5 ng/mL threshold, and the relapse protection window extends farther in the positive direction.

Regarding FIG. 5, the simulations depict the decay in paliperidone plasma concentrations after stopping steady-state dose administrations of: 1) Oral paliperidone ER, 12 mg; 2) PP1M 150 mg eq.; 3) PP3M 525 mg eq.; and 4) PP6M 1000 mg eq.; using the high dose level for each formulation as a representative scenario. Median time to relapse was calculated from the placebo group from the following studies: oral paliperidone ER (R076477SCH301), PP1M (R092670PSY3001), and PP3M (R092670PSY3012) based on the final Kaplan-Meier estimates.

Therefore, a dosing window of up to 2 weeks earlier and up to 3 weeks later than the target 6-month date for maintenance treatment with PP6M is possible and provides scheduling flexibility and enhances treatment adherence, without loss of efficacy or worsening of side effects.

Example 8: Missed Dosing

Based on population pharmacokinetic simulations, the following guidelines are provided in the event of missed doses of PP6M beyond the dosing-window: If more than 6 months and 3 weeks up to but less than 8 months have elapsed since the last injection of PP6M, the following re-initiation regimen may be used.

TABLE 14

Re-initiation Regimen After Missing over 6 Months and 3 Weeks up to but less than 8 Months of PP6M

| If the Last Dose of PP6M was | Administer PP1M into deltoid muscle Day 1 | Then administer PP6M into gluteal muscle 1 month later 1 month after Day 1 |
|---|---|---|
| 1092 mg (700 mg eq.) | 156 mg (100 mg eq.) | 1092 mg (700 mg eq.) |
| 1560 mg (1000 mg eq.) | 234 mg (150 mg eq.) | 1560 mg (1000 mg eq.) |

If 8 months up to and including 11 months have elapsed since the last injection of PP6M, the following re-initiation regimen may be used.

TABLE 15

Re-initiation Regimen After Missing over 8 Months up to 11 Months of PP6M

| If the last dose of PP6M was: | Administer PP1M into deltoid muscle | | Then administer PP6M into gluteal muscle 1 month after Day 8 |
|---|---|---|---|
| | Day 1 | Day 8 | |
| 1092 mg (700 mg eq.) | 156 mg (100 mg eq.) | 156 mg (100 mg eq.) | 1092 mg (700 mg eq.) |
| 1560 mg (1000 mg eq.) | 156 mg (100 mg eq.) | 156 mg (100 mg eq.) | 1560 mg (1000 mg eq.) |

If more than 11 months have elapsed since the last injection of PP6M, re-initiate treatment with PP1M as described in prescribing information for the PP1M product. PP6M can then be resumed after the patient has been adequately treated with PP1M for at least 4 months. To establish a consistent maintenance dose, it is recommended that the last two doses of PP1M should be the same dose strength before re-starting PP6M.

Figure 6:
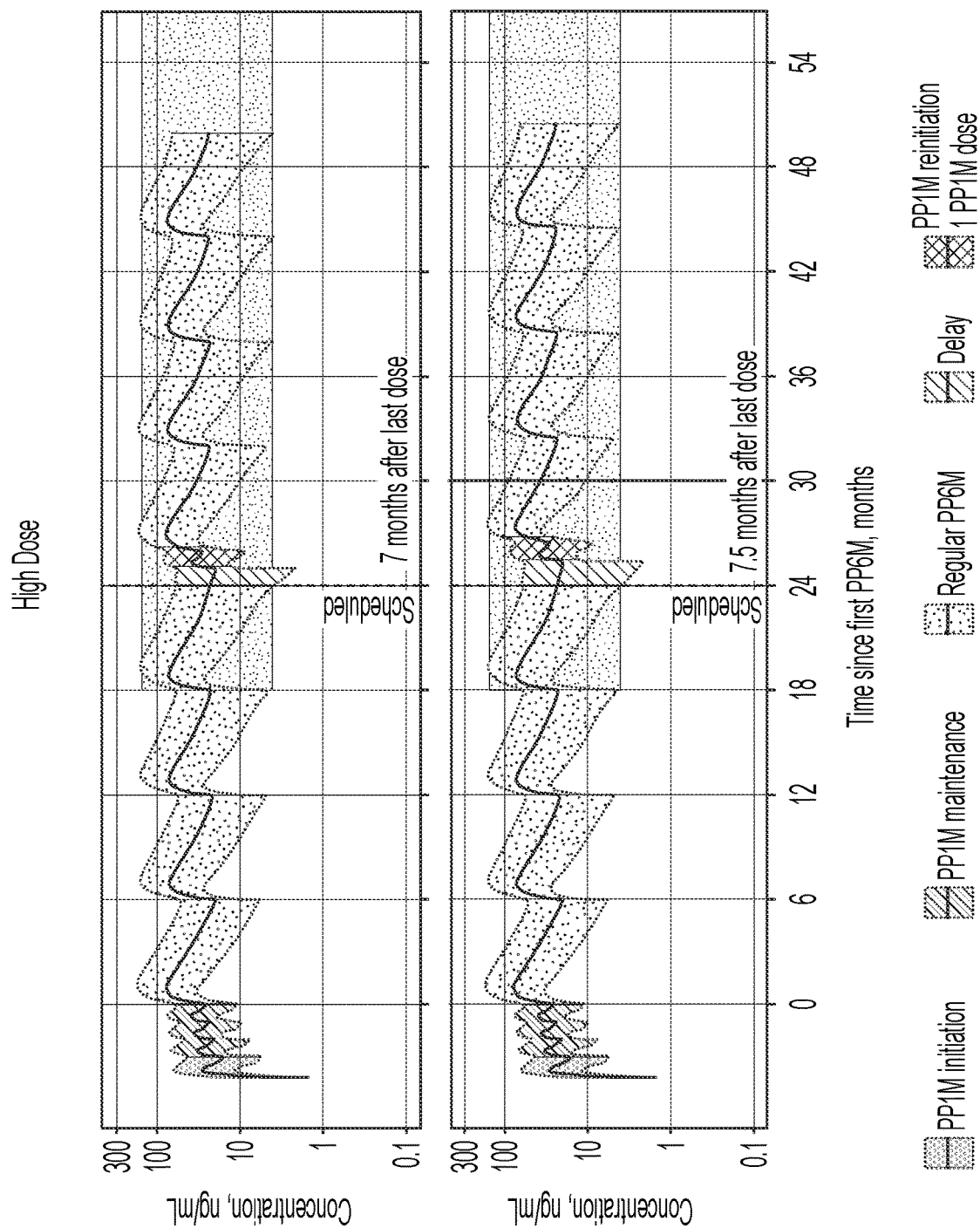
FIG. 6 depicts missed dose simulations for when >6 months and 3 weeks and up to 8 months have elapsed since the last steady-state 1000 mg eq. PP6M injection (7 months, and 7.5 months after the last PP6M dose).
Figure 7:
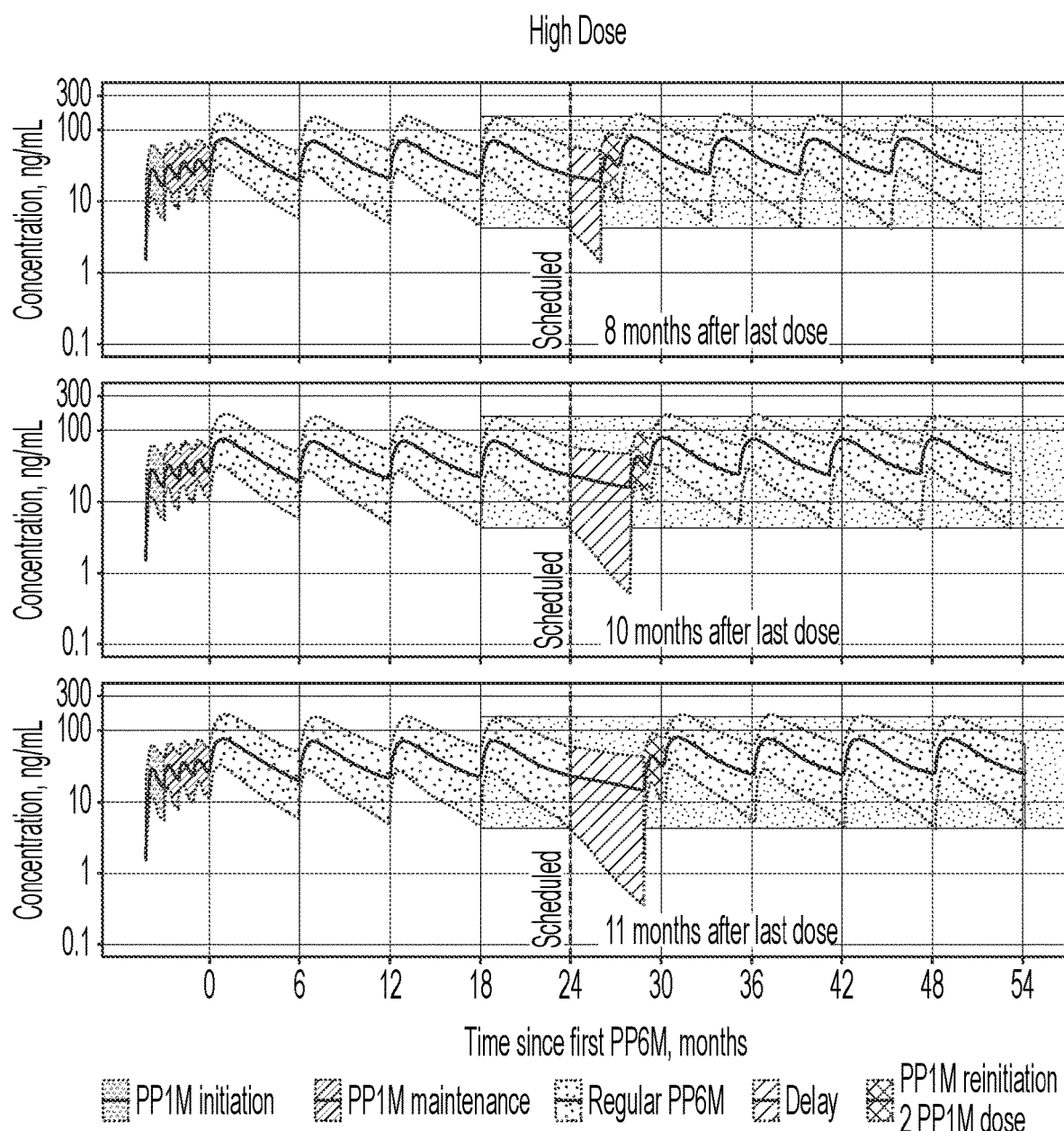
FIG. 7 depicts missed dose simulations when between 8 months up to and including 11 months have elapsed since the last 1000 mg eq. PP6M injection (8, 10 and 11 months after the last PP6M dose).
Figure 8:
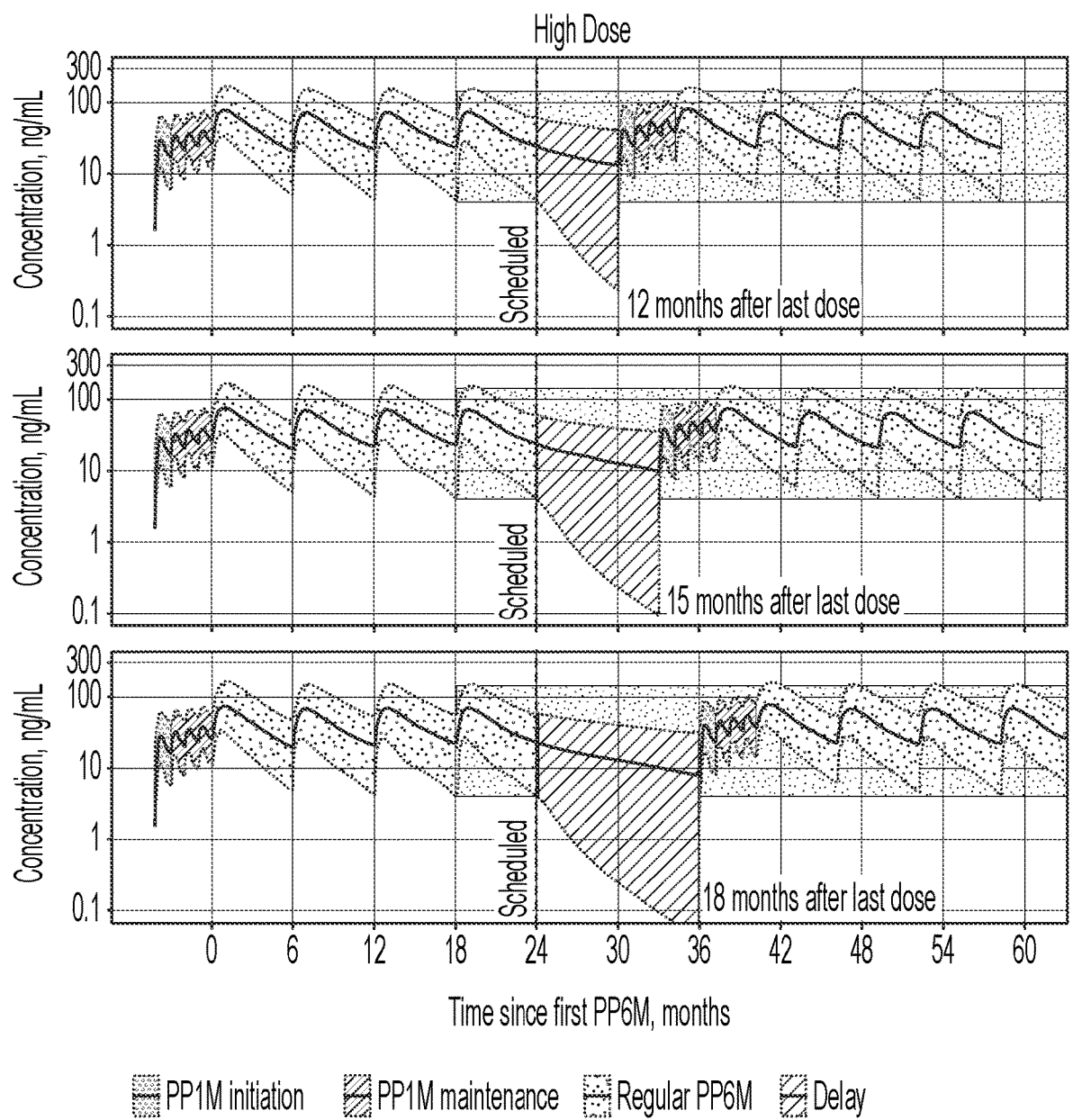
FIG. 8 depicts missed dose simulations for when >11 months have elapsed since the last 1000 mg eq. PP6M injection (12, 15 and 18 months after the last PP6M dose).

The re-initiation regimen after missed dosing and the timing of continuation of the PP6M maintenance regime depends on the time interval since the last PP6M dose. These recommendations are based on simulations performed to address the scenario of a missed dose in patients that have been stabilized on treatment with PP6M, as shown in FIGS. 6-8. Criteria were to achieve a quick return to paliperidone plasma concentrations as before the missed dose, without creating an overshoot due the applied re-initiation regimen.

Regarding FIG. 6, the middle solid line represents the median paliperidone concentration and the shaded area between the bottom and top dotted lines represents the 90% prediction band. Standard PP1M 4-month treatment in deltoid (initiation doses followed by maintenance doses) followed by PP6M dosing. The delay in the last PP6M dose is indicated, and re-initiation, performed with one dose of 150 mg eq. PP1M in deltoid for the high dose level, is indicated. The light stipple area represents the range from trough to peak concentration (defined by the 90% prediction band) before the PP6M dosing interval changed.

Regarding FIG. 7, the middle solid line represents the median paliperidone concentration and the shaded area between the bottom and top dotted lines represents the 90% prediction band. Standard PP1M 4-month treatment in deltoid (initiation doses followed by maintenance doses) followed by PP6M dosing. The delay in the last PP6M dose is indicated, and re-initiation, performed with two doses of 100 mg eq. PP1M in deltoid, is indicated. The light stipple area represents the range from trough to peak concentration (defined by the 90% prediction band) before the PP6M dosing interval changed.

Regarding FIG. 8, the middle solid line represents the median paliperidone concentration and the shaded area between the bottom and top dotted lines represents the 90% prediction band. Standard PP1M 4-month treatment in deltoid (initiation doses followed by maintenance doses) followed by PP6M dosing. The delay in the last PP6M dose is indicated, and re-initiation is performed as a 4-month PP1M treatment in deltoid. The light stipple area represents the range from trough to peak concentration (defined by the 90% prediction band) before the PP6M dosing interval changed.

These guidelines provide a mechanism by which patients can resume treatment with PP6M in case they become fully or partially non-adherent, thereby reducing the need to start treatment de novo.

Example 9—Weight Change Associated with PP6M Treatment

Figure 9:
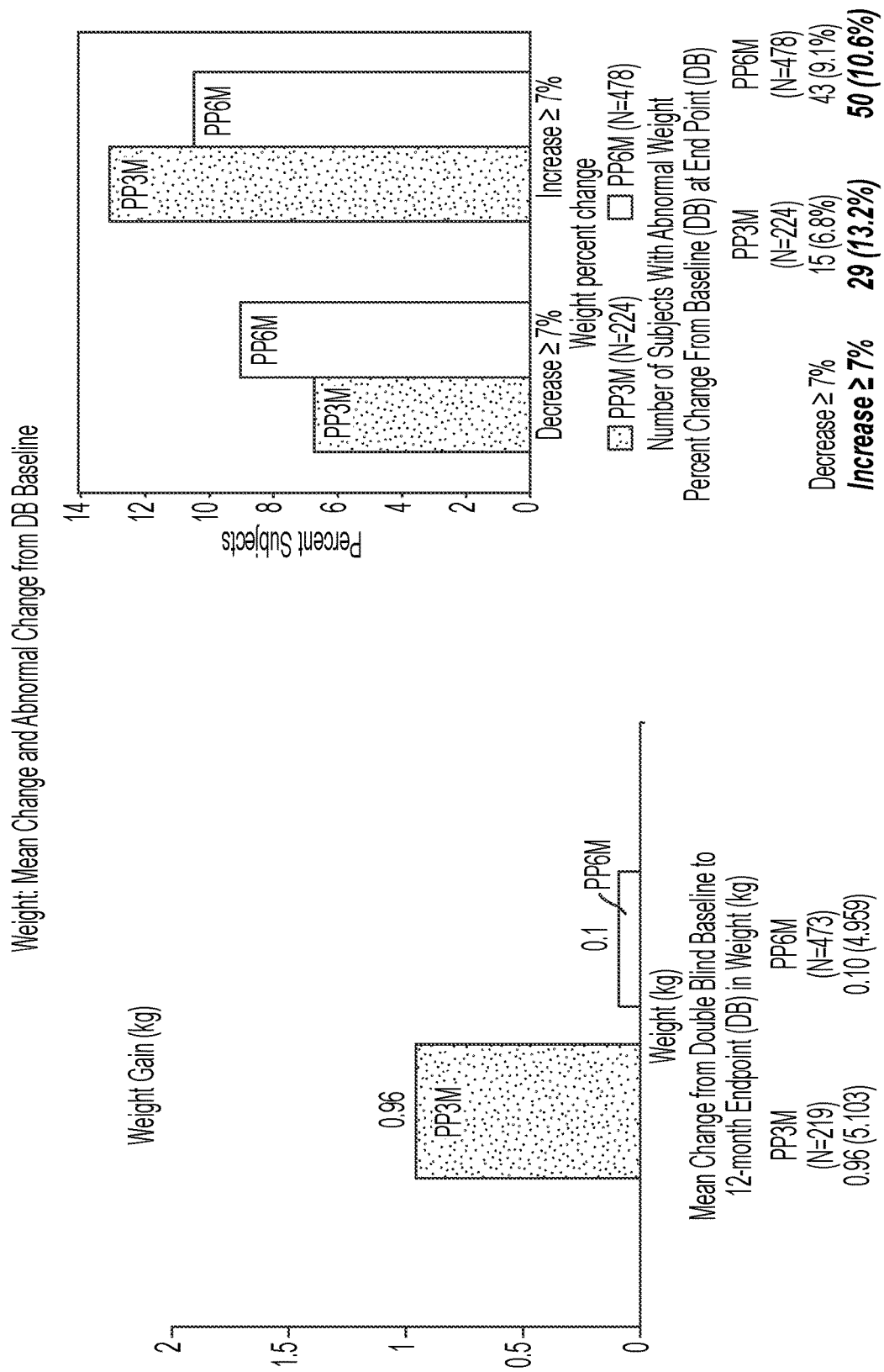
FIG. 9 depicts bar graphs showing mean weight change and abnormal weight change from double-blind baseline for patients treated with PP6M.

Based on the findings of the studies set forth in Example 4, patients with schizophrenia stabilized on shorter acting paliperidone formulations (PPIM, PP3M) who were switched to the longer acting formulation (PP6M) showed substantially less overall weight gain during double-blind phase (12 months) and more weight loss compared to patients treated with PP3M (active comparator) during the 12 month double-blind phase, as shown in FIG. 9. For example, the weight gain in the patient population of PP6M was negligible (0.1 kg in 12 months, left graph of FIG. 9) and a higher percentage of patients showed a major weight loss of over 7% of their body weight (right graph of FIG. 9).

Figure 10:
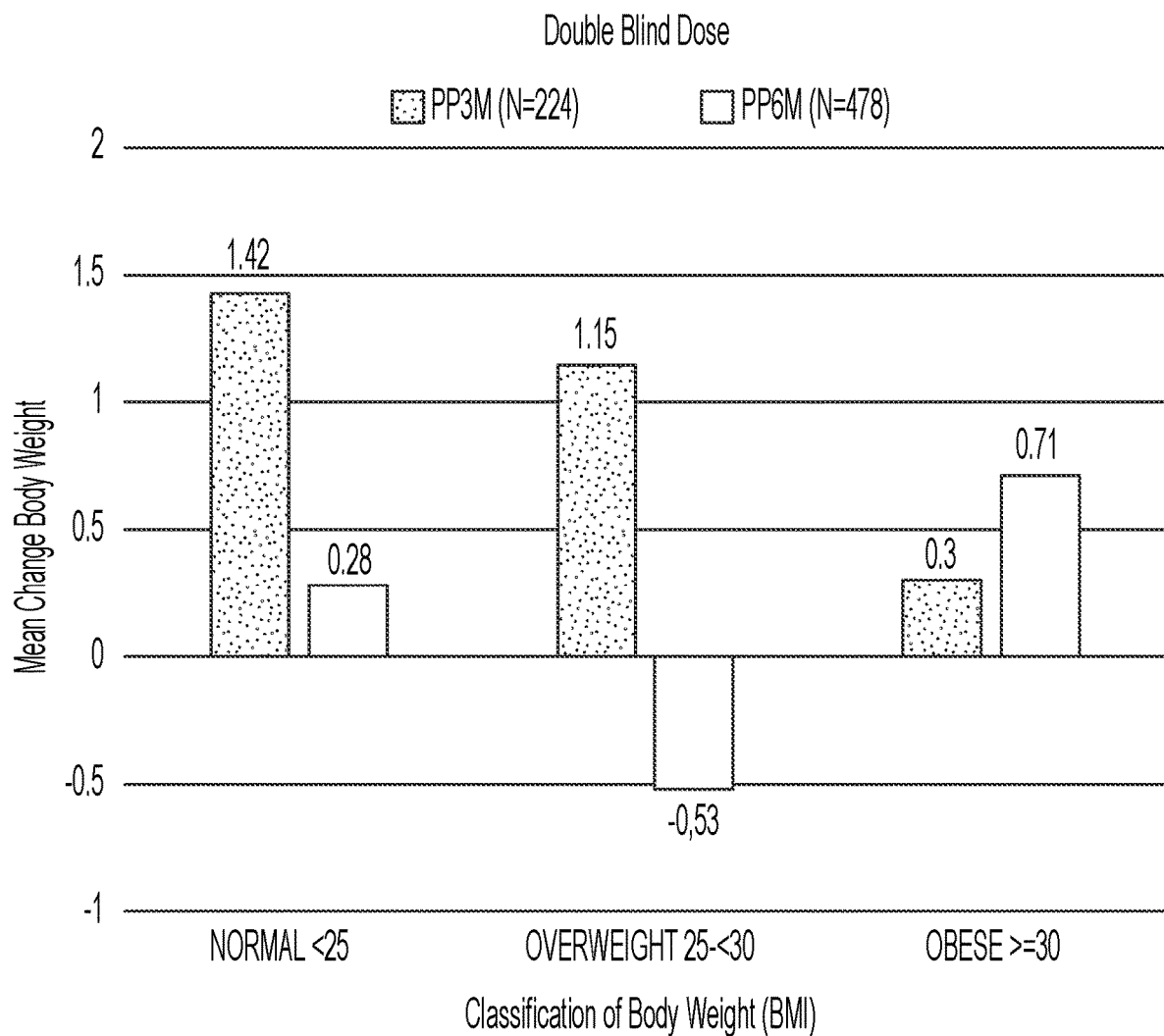
FIG. 10 depicts a bar graph showing mean weight change of patients of various weight class (normal, overweight and obese) being treated with PP6M.
Figure 11:
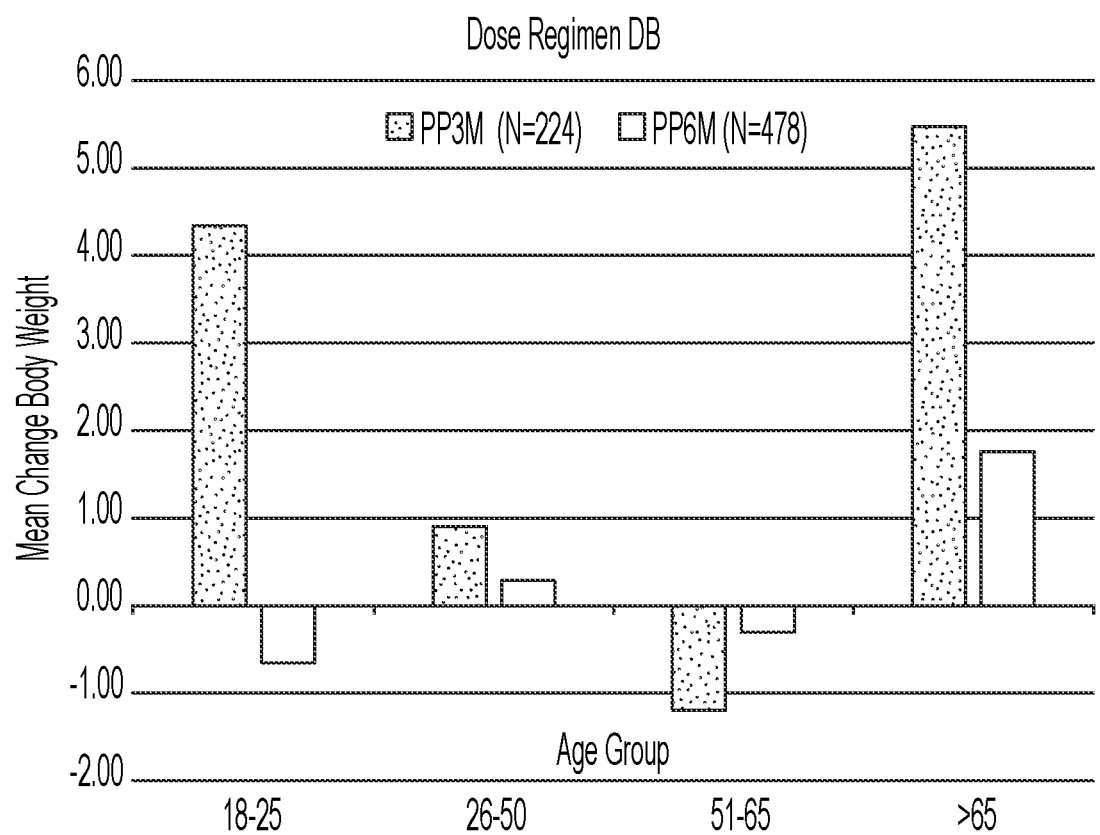
FIG. 11 depicts a bar graph showing mean weight change of patients of various age groups being treated with PP6M.

The data was further analyzed and found that overweight patients (BMI between 25 and <30) received a benefit from being switched to PP6M (FIG. 10) as did patients in the age group 18-25 (FIG. 11). While showing a beneficial effect on weight, the studies also showed non-inferior efficacy of PP6M compared to PP3M on the primary endpoint of time to relapse at the end of the 12-month period in both intent-to-treat and per-protocol analysis sets. The safety profile observed for PP6M was consistent with previous studies of PP1M and PP3M formulations with no new safety signals emerging.

As most of the weight gain was reported at the double-blind baseline (day 1) of the study indicating that weight increase occurred during the open label stabilizing phase. There was no incremental weight gain noted during the double-blind phase (12 month) suggesting a stabilizing effect on mean weight gain with more infrequent injections.

Therefore, patients with increasing weight could be switched to PP6M to help stabilize their weight or to support a body weight decrease.

From baseline (DB) to double blind end point, the changes in body weight, waist circumference, and BMI were numerically higher in the PP3M group versus the PP6M group. The mean (SD) increases from baseline (MA) to Double-blind end point in body weight were 0.10 (4.959) kg and 0.96 (5.103) kg for the PP6M and PP3M groups, respectively.

From DB baseline to double-blind end point, 10.6% of subjects in the PP6M group and 13.2% of subjects in the PP3M group experienced an abnormal increase in body weight (>7%). 9.1% of subjects in the PP6M group and 6.8% of subjects in the PP3M group experienced an abnormal decrease in body weight (≥7%) from DB baseline to Double-blind end point.

Regarding FIG. 10, the mean (SD) change by baseline (DB) BMI was 0.28 (3.404) kg in the PP6M group and 1.42 (4.456) kg in the PP3M group for subjects with normal (<25) baseline BMI; −0.53 (4.386) kg in the PP6M group and 1.15 kg (4.814) kg in the PP3M group for over-weight (BMI 25 to <30) subjects; and 0.71 (6.448) kg in the PP6M group and 0.30 (5.955) kg in the PP3M group for obese (BMI>30) subjects.

Regarding FIG. 11, the mean (SD) change by age was −0.65 (4.955) kg in the PP6M group and 4.33 (7.112) kg in the PP3M group for subjects in the 18 to 25 years age group; 0.29 (4.878) kg in the PP6M group and 0.91 (4.600) kg in the PP3M group for subjects in the 25 to 50 years age group; −0.31 (5.247) kg in the PP6M group and −1.20 (4.763) kg in the PP3M group for subjects in the 51 to 65 years age group; and 1.76 (4.738) kg in the PP6M group and 5.47 (5.707) kg for subjects >65 years.

What is claimed is:

1. A method for administering paliperidone palmitate to a patient in need of treatment for psychosis, schizophrenia, schizoaffective disorder, schizophreniform disorder, or bipolar disorder who has been administered a first dose of a six-month paliperidone palmitate extended-release injectable suspension (PP6M), comprising administering a second dose of the PP6M to a deltoid or gluteal muscle of the patient within a dosing window of a dosing regimen for the PP6M that is up to two weeks before or three weeks after a time that is six months after administration of the first dose such that the patient has not missed a dose based on the regimen, wherein there is no intervening dose of paliperidone palmitate between the first dose and the second dose;
wherein the first dose and the second dose each comprise about 1092 mg paliperidone palmitate; and
wherein the PP6M comprises about 280 mg/mL to about 350 mg/mL of the paliperidone palmitate.

2. The method of claim 1, wherein the patient has a steady state paliperidone plasma concentration at the time of the first dose.

3. The method of claim 1, wherein the patient is in need of treatment for schizophrenia.

4. The method of claim 3, wherein the first and second dose of PP6M are administered to a gluteal muscle of the patient.

5. The method of claim 4, wherein the PP6M further comprises:
about 8 mg/mL to about 12 mg/mL of a wetting agent;
one or more buffering agents;
about 65 mg/mL to about 85 mg/mL of a suspending agent;
and water q.s. ad 100%.

6. The method of claim 5, wherein the PP6M is from about pH 6.0 to about pH 8.0.

7. The method of claim 5, wherein the one or more buffering agents comprise citric acid monohydrate, sodium dihydrogen phosphate monohydrate, disodium hydrogen phosphate anhydrous, or sodium hydroxide.

8. The method of claim 5, wherein the PP6M comprises:
about 312 mg/mL of paliperidone palmitate;
about 10 mg/mL of the wetting agent, wherein the wetting agent is polysorbate 20; and
about 75 mg/mL of the suspending agent, wherein the suspending agent is polyethylene glycol 4000.

9. The method of claim 4, wherein the PP6M comprises about 312 mg/mL of paliperidone palmitate.

10. A method for administering paliperidone palmitate to a patient in need of treatment for psychosis, schizophrenia, schizoaffective disorder, schizophreniform disorder, or bipolar disorder who has been administered a first dose of a six-month paliperidone palmitate extended-release injectable suspension (PP6M), comprising administering a second dose of the PP6M to a deltoid or gluteal muscle of the patient within a dosing window of a dosing regimen for the PP6M that is up to two weeks before or three weeks after a time that is six months after administration of the first dose such that the patient has not missed a dose based on the regimen,
wherein there is no intervening dose of paliperidone palmitate between the first dose and the second dose;
wherein the first dose and the second dose each comprise about 1560 mg paliperidone palmitate; and
wherein the PP6M comprises about 280 mg/mL to about 350 mg/mL of the paliperidone palmitate.

11. The method of claim 10, wherein the patient is in need of treatment for schizophrenia.

12. The method of claim 11, wherein the first and second dose of PP6M are administered to a gluteal muscle of the patient.

13. The method of claim 12, wherein the PP6M comprises about 312 mg/mL of paliperidone palmitate.

14. The method of claim 12, wherein the PP6M further comprises:
about 8 mg/mL to about 12 mg/mL of a wetting agent;
one or more buffering agents;
about 65 mg/mL to about 85 mg/mL of a suspending agent;
and water q.s. ad 100%.

15. The method of claim 14, wherein the PP6M is from about pH 6.0 to about pH 8.0.

16. The method of claim 14, wherein the one or more buffering agents comprise citric acid monohydrate, sodium dihydrogen phosphate monohydrate, disodium hydrogen phosphate anhydrous, or sodium hydroxide.

17. The method of claim 14, wherein the PP6M comprises:
about 312 mg/mL of paliperidone palmitate;
about 10 mg/mL of the wetting agent, wherein the wetting agent is polysorbate 20; and
about 75 mg/mL of the suspending agent, wherein the suspending agent is polyethylene glycol 4000.

18. The method of claim 10, wherein the patient has a steady state paliperidone plasma concentration at the time of the first dose.

* * * * *